(12) United States Patent
Roman et al.

(10) Patent No.: US 6,395,781 B1
(45) Date of Patent: May 28, 2002

(54) 20-HETE ANTAGONISTS AND AGONISTS

(75) Inventors: Richard J. Roman, Brookfield, WI (US); John R. Falck, Dallas, TX (US); Magdalena Alonso-Galicia, New Berlin, WI (US); Elizabeth R. Jacobs, Milwaukee, WI (US); David R. Harder, Waukesha, WI (US)

(73) Assignee: MCW Research Foundation, Milwaukee, WI (US)

( * ) Notice: Subject to any disclaimer, the term of this patent is extended or adjusted under 35 U.S.C. 154(b) by 0 days.

(21) Appl. No.: 09/259,414

(22) Filed: Feb. 23, 1999

Related U.S. Application Data

(60) Provisional application No. 60/076,091, filed on Feb. 26, 1998.

(51) Int. Cl.$^7$ .............................................. A61K 31/20
(52) U.S. Cl. ...................... 514/560; 514/381; 514/382; 514/417; 514/423; 514/558; 514/559; 514/601; 514/602; 514/603; 514/604; 514/605; 514/613; 514/616; 514/671; 514/675; 514/678; 514/706; 514/713; 514/731; 514/733; 514/738; 514/739; 514/627; 514/826; 514/866
(58) Field of Search .................. 514/560, 559, 514/558, 601, 602, 604, 605, 706, 713, 613, 616, 627, 675, 678, 731, 733, 738, 739, 826, 866, 671, 381, 382, 417, 423

(56) References Cited

U.S. PATENT DOCUMENTS

| | | | |
|---|---|---|---|
| 5,334,736 A | 8/1994 | Sun et al. | 554/148 |
| 5,753,702 A | 5/1998 | Bednar et al. | 514/552 |

FOREIGN PATENT DOCUMENTS

| | | |
|---|---|---|
| WO | WO 97/44024 A | 11/1997 |

OTHER PUBLICATIONS

"Inhibition of 20–HETE Production Contributes to the Vascular Responses to Nitric Oxide," M. Alonso–Galicia, H.A. Drummond, K.K. Reddy, J.R. Falck and R.J. Roman, *Hypertension*, 29:320–25. (1997).
"Human pulmonary arties dilate to 20–HETE, an endogenous eicosanoid of lung tissue," E.K. Birks, M. Bousamra, K. Presberg, J.A. Marsh, R.M. Effros and E.R. Jacobs, Publ. No. 1040–0605/97 (1997), the American Physiological Society.
"Identification of a Putative Microvascular Oxygen Sensor," D.R. Harder, J. Narayanan, E.K. Birks, J.F. Liard, J.D. Imig, J.H. Lombard, A.R. Lange and R.J. Romain, *Circulation Research*, 79:54–61 (Jul. 1996).
"Cytochrome P450 Metabolites of Arachidonic Acid as Intracellular Signaling Molecules in Vascular Tissue," D.R. Harder, A.R. Lange, D. Gebremedhin, E.R. Birks and R.J. Roman, *J. Vasc. Res.*, 34:237–243 (1997).
"Formation and actions of 20–hydroxyeicosatetraenoic acid in rat renal arterioles," J.D. Imig, A. Zou, D.E. Stec, D.R. Harder, J.R. Falck and R.J. Roman, Publ. No. 0363–6119/96 (1996), the American Physiological Society.
"Cytochrome P4504A Genotype Cosegregates with Hypertension in Dahl S Rats," D.E. Stec, A.Y. Deng, J.P. Rapp and R.J. Roman, *Hypertension*, 27:564–568 (Mar. 1996).
"Renal Cytochrome P4504A Activity and Salt Sensitivity in Spontaneously Hypertensive Rats," D.E. Stec, M.R. Trolliet, J.E. Krieger, H.J. Jacob and R.J. Roman, *Hypertension*, 27:1329–1336 (Jun. 1996).
"Effect of P–450 ω–hydroxylase metabolites of arachidonic acid on tubuloglomerular feedback," A. Zou, J.D. Imig, P.R. Ortiz de Montellano, Z. Sui, J. Falck and R.J. Roman, Publ. No. 0363–6127/94 (1994), the American Physiological Society.
"Effects of 17–Octadecynoic Acid, a Suicide–Substrate Inhibitor of Cytochrome P450 Fatty Acid ω–Hydroxylase, on Renal Function in Rats," A. Zou, Y. Ma, Z. Sui, P.R. Ortiz, J.E. Clark, B.S. Masters and R.J. Roman, *J. Pharm. & Exper. Therap.*, 268:474–481. (1996).
M. Alonso–Galicia, et al., "Inhibition of 20–HETE Production Contributes to the Vascular Responses to Nitric Oxide," *Hypertension* 29(1):325–325, 1997.
M. Alonso–Galicia, et al., "Structural Determinants of the Renal Vascular Response to 20–Hydroxyeicosatetraenoic Acid (20–HETE)," *FASEB J.* 11:A244, 1997.
Burhop, et al., "Monohydroxyeisosatetraenoic Acids (5–HETE and 15–HETE) Induce Pulmonary Vasoconstriction and Edema," *Circ. Res.* 62(4):687–698, 1988.
Imig, et al., "Formation and Actions of 20–HETE in rat renal arterioles," *Am. J. Physiol.* 270(1):217–227, 1996 (Abstract).
Elizabeth R. Jacobs, et al., "Airway Synthesis of 20–Hydroxyeicosatetraenoic Acid: Metabolism by Cyclooxygenase to a Bronchodilator," *Am. Physiol. Soc.* L280–L288, 1999.
Lange, et al., "20–HETE–induced Vasoconstriction and Inhibition of Potassium Current in Cerebral Vascular Smooth Muscle is Dependent on Activation of Protein Kinase C," *J. Biol. Chem.* 272(43):27345–27352, 1997 (Abstract).
Ma, et al., "20–HETE is an Endogenous Vasoconstrictor of Canine Renal Arcuate Arteries," *Circ. Res.* 72(1):126–136, 1993 (Abstract).
Omata, et al., "Roles of Renal Cytochrome P450–dependent Arachidonic Acid Metabolites in Hypertension," *Tohoku J. Exp. Med.* 166(1):93–106, 1992.
Cheng–Wen Sun, et al., "Nitric Oxide–20–Hydroxyeicosatetraenoic Acid Interaction in the Regulation of K$^+$ Channel Activity and Vascular Tone in Renal Arterioles," *Circ. Res.* pp. 1069–1079, 1998.

*Primary Examiner*—Frederick Krass
(74) *Attorney, Agent, or Firm*—Quarles & Brady LLP

(57) ABSTRACT

20-HETE agonists and antagonists are disclosed along with therapeutic applications. In a preferable form of the invention, the 20-HETE agonists are selected from the group consisting of 21-hydroxyheneicosa-5(Z),8(Z),11(Z),14(Z)-tetraenoic acid, 20-hydroxyeicosa-5(Z),14(Z)-dienoic acid and 20-,21-dimethyl 20-HETE. Preferable 20-HETE antagonists include 5(S)-HETE, 15(S)-HETE, 19(S)-HETE, 19-hydroxynonadeca-5(Z),8(Z),11(Z),14(Z)-tetraenoic acid and 20-hydroxyeicosa 6(Z),15(Z)-dienoic acid.

17 Claims, 17 Drawing Sheets

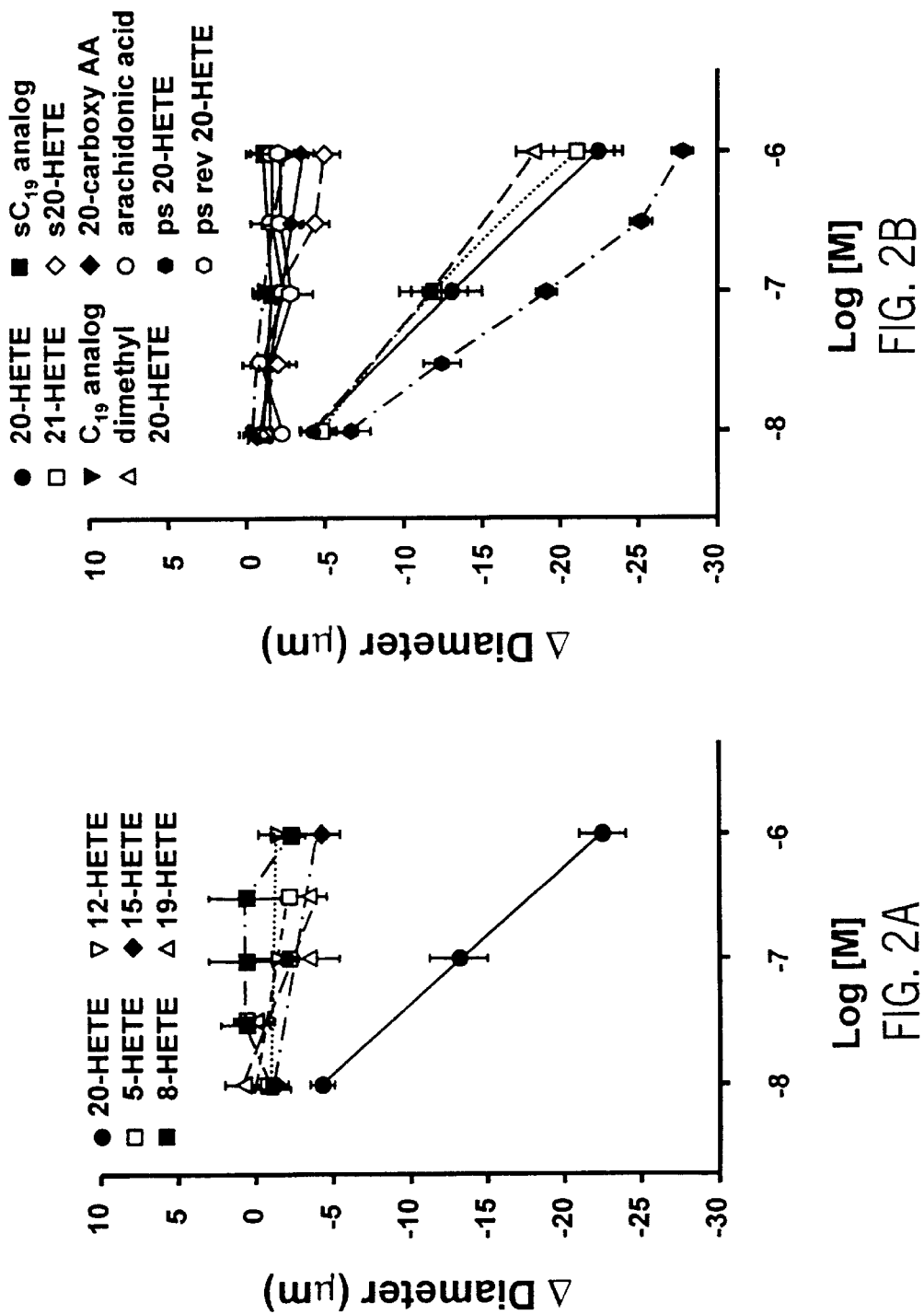

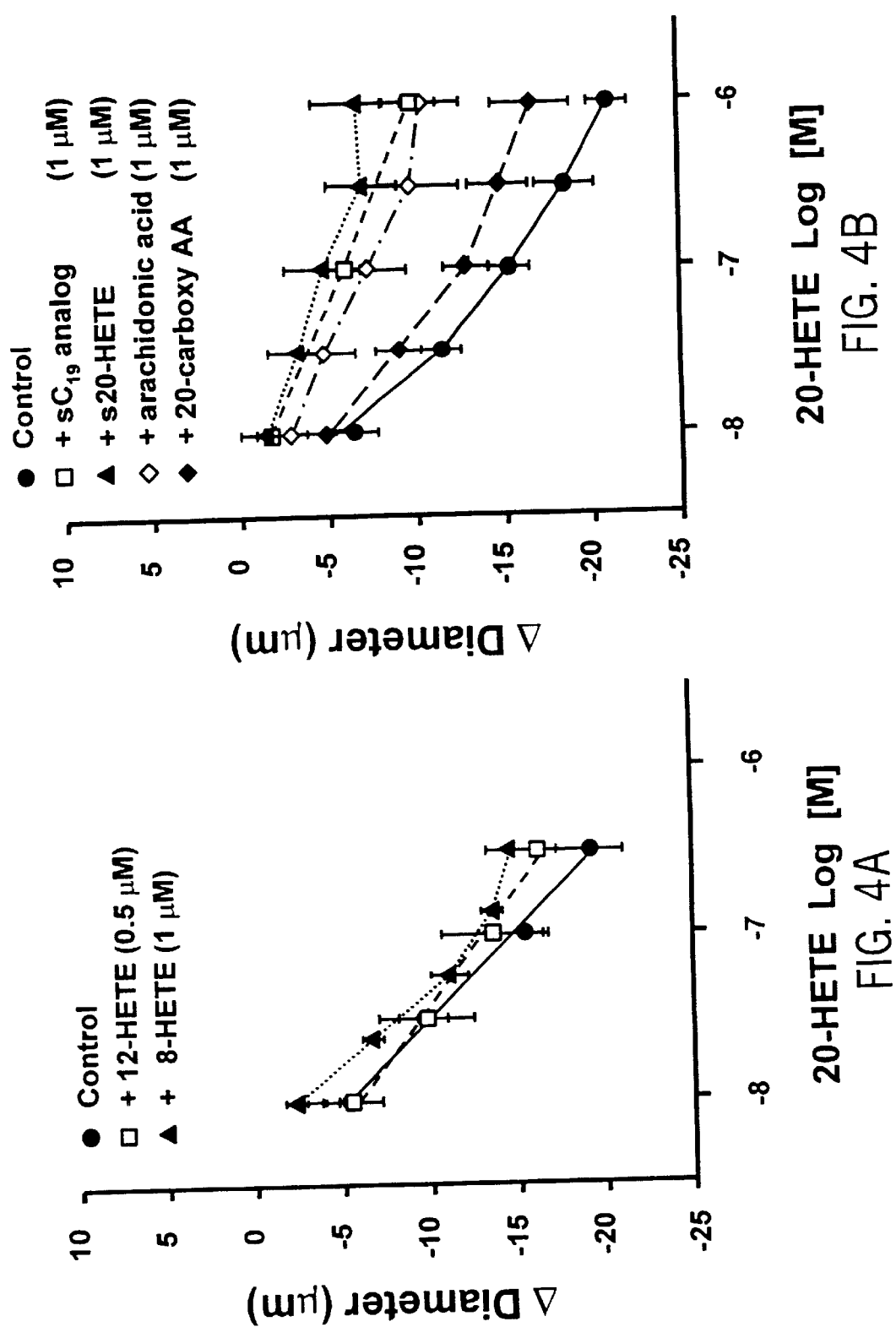

Agonists
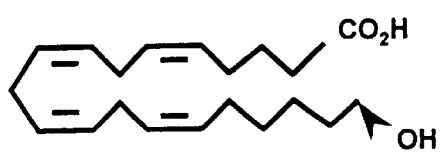
20-HETE
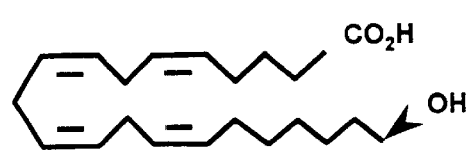
21-HETE
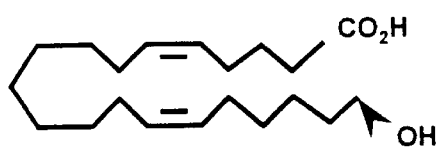
ps 20-HETE
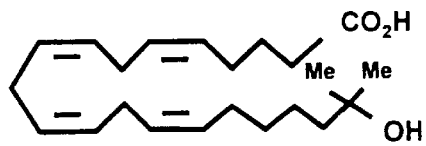
Dimethyl 20-HETE
Antagonists
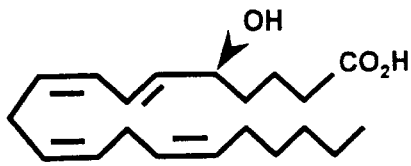
5(S)-HETE
15(S)-HETE
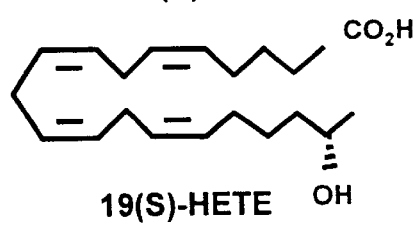
19(S)-HETE
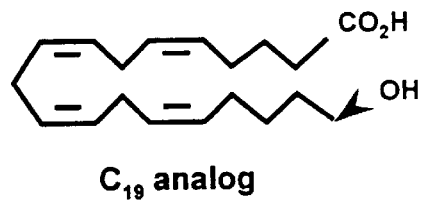
C$_{19}$ analog
Ps rev 20-HETE
FIG. 5

Conceptualized 20-HETE agonist/antagonist

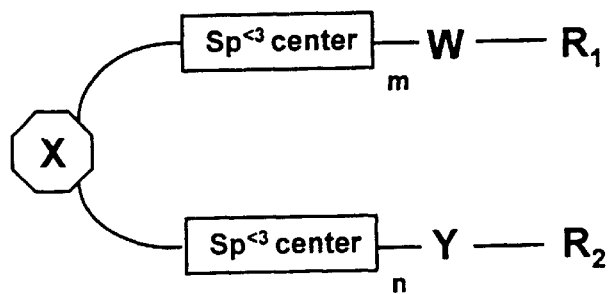

$R_1$ = carboxylic acid; phenol; amide; imide; sulfonamide; sulfonimide; active methylene; 1,3-dicarbonyl; alcohol; thiol; amine; tetrazole or other heteroaryl.

$R_2$ = carboxylic acid; phenol; amide; imide; sulfonamide; sulfonimide; active methylene; 1,3-dicarbonyl; alcohol; thiol; amine; tetrazole or other heteroaryl.

W = carbon chain ($C_1$ through $C_{25}$) either linear, cyclic, or branched with or without heteroatoms such as S, O, N, Se; aryl; heteroaryl.

Y = carbon chain ($C_1$ through $C_{25}$) either linear, polycyclic, or branched with or without heteroatoms such as S, O, N, Se; aryl; heteroaryl.

$Sp^{<3}$ center = vinyl; aryl; heteroaryl; cyclopropyl; acetylenic.

X = alkyl (linear, branched, cyclic, polycyclic) with or without heteroatoms; vinyl; aryl; heteroaryl; cyclopropyl; acetylenic.

Conceptualized 20-HETE agonist and/or antagonist
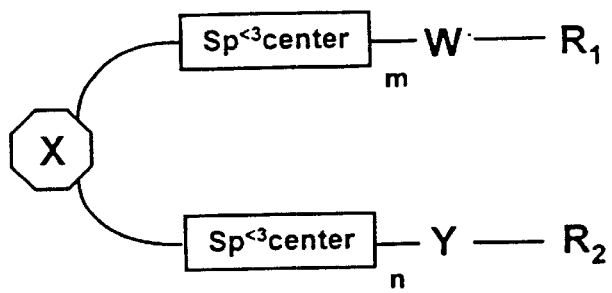
Examples of 20-HETE agonist and/or antagonist
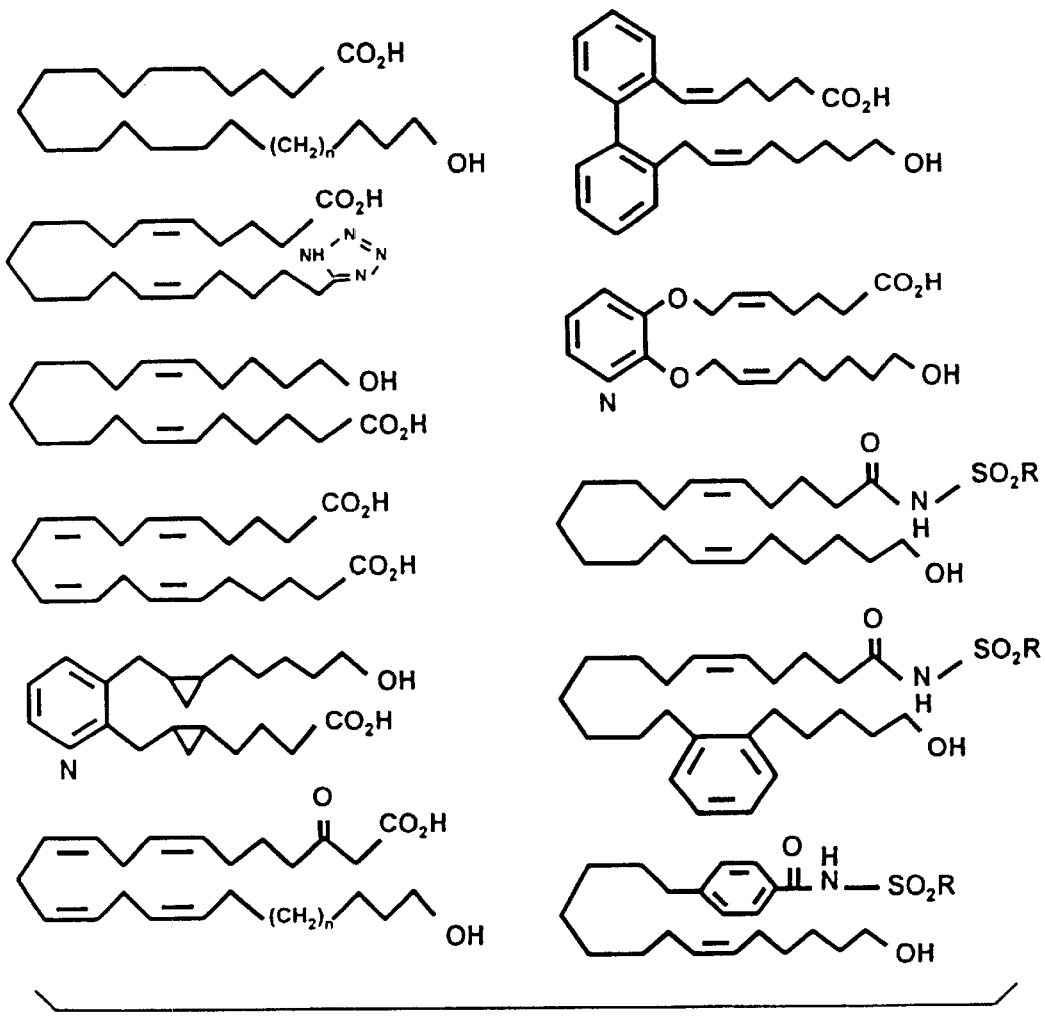
FIG. 7A

Conceptualized 20-HETE agonist and/or antagonist
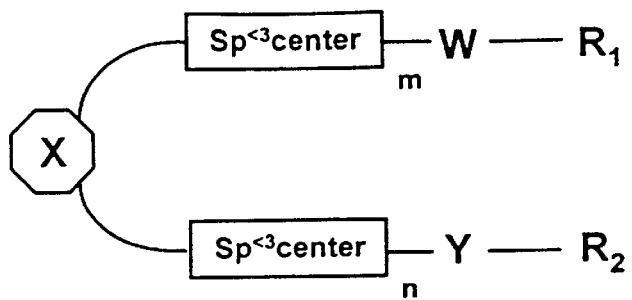
Examples of 20-HETE agonist and/or antagonist
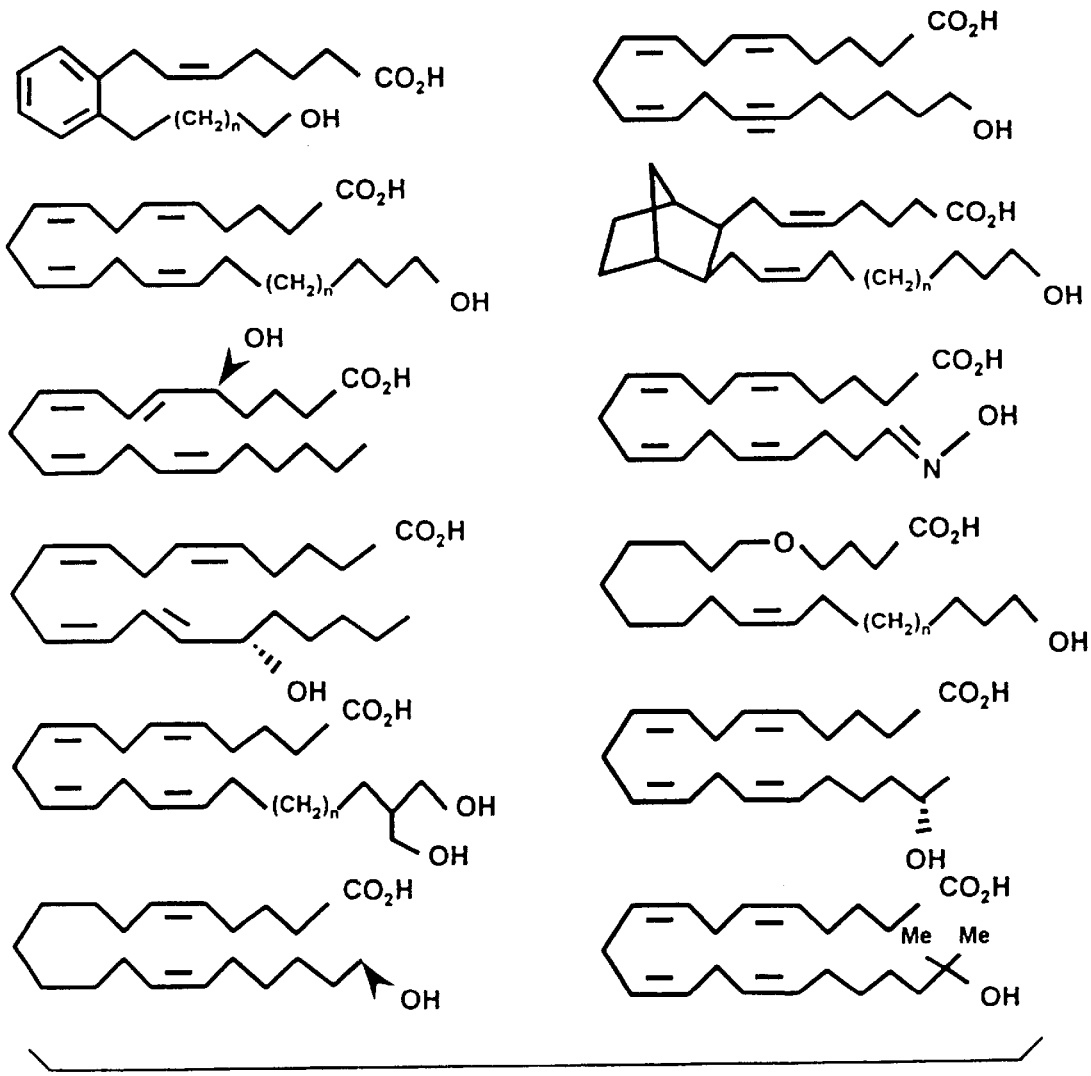
FIG. 7B

20-HETE ANTAGONISTS AND AGONISTS

CROSS-REFERENCE TO RELATED APPLICATION

This application claims priority from U.S. Ser. No. 60/076,091, filed Feb. 26, 1998, incorporated by reference.

STATEMENT REGARDING FEDERALLY SPONSORED RESEARCH OR DEVELOPMENT

This work was supported in part from Grants HL-29587, HL-36279 and GM 31278 from the National Institutes of Health. The U.S. Government may have certain rights to this invention.

BACKGROUND OF THE INVENTION

Recent studies have indicated that vascular smooth muscle cells in a variety of vascular beds express enzymes of the cytochrome P450 4A and related families (CYP 4A) that catalyze the formation of 20-hydroxyeicosatetraenoic acid (20-HETE). 20-HETE is a potent constrictor ($EC_{50} < 10^{-8}$ M) of renal, cerebral and skeletal muscle arterioles. It promotes $Ca^{2+}$ entry by depolarizing VSM cells secondary to blockade of $K_{Ca}$ channels and by increasing the conductance of L-type $Ca^{2+}$ channels (Harder, D., *J. Vasc. Research* 34:237–243, 1997; Roman, R., *News in Physiological Sciences*, 1999, in press). In the kidney, 20-HETE is also produced by renal tubular cells where it participates in the regulation of sodium transport in the proximal tubule and thick ascending limb of the loop of Henle. In (Roman R., Supra, 1999) human and rabbit lung, 20-HETE is also produced by the airways where it serves as an potent endogenously produced bronchodilator (Zhu, D., *Am. J. Resp. Cell Mol. Biol.* 19:121–128, 1998; Jacobs, E. R., *Am. J. Physiol.* 1999, in press).

Despite the importance of 20-HETE in the regulation of vascular tone, kidney function, and airway resistance, little is known of its mechanism of action. Recent studies have indicated that the vasoconstrictor response to 20-HETE and its inhibitory actions on sodium transport is associated with activation of PKC and MAP kinase signal transduction cascades(Sun, C. -W., *Hypertension* 33:414–418, 1999). Activation of these pathways are usually triggered by receptor mediated events, however, at present time there is no evidence for a 20-HETE receptor. To date, there have been no published studies to determine whether 20-HETE binds to membrane or cytosolic proteins or to determine whether the vasoconstrictor response is specific to 20-HETE or can be mimicked by closely related analogs.

BRIEF SUMMARY OF THE INVENTION

The present invention springs from a study designed to perform structure activity studies with a series of 20-HETE analogs to determine the structural determinants to the vasoconstrictor response in interlobular arteries microdissected from the kidney of rats.

In one embodiment, the invention is a method of reducing a patient's vascular diameter or preventing 20-HETE from reducing vascular diameter, comprising the step of supplying to the patient an effective amount of a 20-HETE agonist or antagonist.

Preferably, the compound is of the following formula:

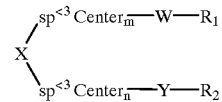

$R_1$ is selected from the group consisting of carboxylic acid; phenol; amide; imide; sulfonamide; sulfonimide; active methylene; 1,3-dicarbonyl; alcohol; thiol; amine; tetrazole or other heteroaryl;

$R_2$ is selected from the group consisting of carboxylic acid; phenol; amide; imide; sulfonamide; sulfonimide; active methylene; 1,3-dicarbonyl; alcohol; thiol; amine; tetrazole or other heteroaryl;

W is a carbon chain ($C_1$ through $C_{25}$) and may be linear, cyclic, or branched and may comprise heteroatoms, such as S, O, N or Se;

Y is a carbon chain ($C_1$ through $C_{25}$) and may be linear, cyclic, or branched and may comprise heteroatoms such as S, O, N or Se;

$sp^{<3}$ Center is selected from the group consisting of vinyl; aryl; heteroaryl; cyclopropyl; and acetylenic moieties;

X is an alkyl (linear, branched, cyclic or polycyclic) group with or without heteroatoms; or a vinyl; aryl; heteroaryl; cyclopropyl; or acetylenic group;

m=0, 1, 2, 3, 4 or 5 and n=0, 1, 2, 3, 4 or 5.

In a preferred embodiment of the method, the compound is an agonist and vascular diameter is reduced or bronchiole smooth muscle is dilated. In this embodiment, the compound is a 20-HETE agonist. Preferably, the agonist compound is selected from the group consisting of 21-hydroxyheneicosa-5(Z),8(Z),11(Z),14(Z)-tetraenoic acid; 20-hydroxyeicosa-5 (Z),14(Z)-dienoic acid; and dimethyl 20-HETE.

In another embodiment of the method, the compound is a 20-HETE antagonist and the vascular diameter is prevented from being reduced by endogenous 20-HETE. Preferably, the compound is selected from the group consisting of 5(S)-HETE; 15(S)-HETE; 19(S)-HETE; 19-hydroxynonadeca-5(Z),8(Z),11(Z),14(Z)-tetraenoic acid ($C_{19}$ analog); and 20-hydroxyeicosa 6(Z),15(Z)-dienoic acid (Ps rev 20-HETE).

In another embodiment, the present invention is a method of treating a patient comprising the steps of supplying an effective amount of a 20-HETE agonist or antagonist.

In another embodiment, the patient has a disease selected from the group consisting of diabetes, toxemia of pregnancy (preeclampsia), hepatorenal syndrome, cyclosporin-induced nephrotoxicity, cerebral vasospasm, stroke, and hypertension and the vasoconstrictor actions of the patient's excess endogenously-produced 20-HETE is moderated when treated with a 20-HETE antagonist.

In another embodiment, the patient has septic shock or other inflammatory disease associated with induction of nitric oxide synthase and is treated with an amount of 20-HETE antagonist sufficient to reduce symptoms.

In another embodiment, patients are treated with a 20-HETE antagonist to prevent vascularization of granular or neoplastic tissues. This treatment reduces blood supply and prevents growth of tumors.

In another embodiment, the patient has a condition selected from the group of congestive heart failure, pulmonary edema, hepatorenal syndrome and hypertension and is treated with an amount of 20-HETE agonist sufficient to provide a diuretic effect, lower blood volume, and prevent edema.

In another embodiment, the patient has asthma and the 20-HETE agonist is delivered as an inhalational therapy to dilate constricted airways.

In another embodiment, the patient may have pulmonary hypertension and 20-HETE or a 20-HETE agonist is infused to dilate the pulmonary circulation.

In another embodiment, the patient may have cerebral vascular injury, vasospasm, migraine or cluster headaches, stroke or cocaine-induced vasospasm and is treated with a 20-HETE antagonist to increase blood flow and relieve symptoms.

The present invention is also a pharmaceutical preparation comprising a compound selected from the group of 20-HETE agonists and antagonists and a pharmaceutically acceptable carrier. The preparation is preferably selected from the group of the 19-hydroxynonadeca-5(Z),8(Z),11(Z), 14(Z)-tetraenoic acid, 20-hydroxyeicosa 6(Z),15(Z)-dienoic acid, 20 hydroxyeicosa-5(Z),14(Z)-dienoic acid, dimethyl 20-HETE 21-hydroxyheneicosa-5(Z),8(Z),11(Z),14(Z)-tetraenoic acid, N-methylsulfonyl-20-hydroxyeicosa-5(Z), 14(Z)-dienamide, or N-methylsulfonyl-20-hydroxyeicosa-6 (Z),15(Z)-dienamide and a pharmaceutically acceptable carrier.

It is a feature of the present invention that 20-HETE agonists and antagonists are provided. A general formula is also provided describing 20-HETE agonists and antagonists.

It is another feature of the present invention that therapeutic uses of 20-HETE agonists and antagonists are described.

Other features, objects and advantages of the present invention will become apparent after examination of the specification, claims and drawings.

BRIEF DESCRIPTION OF THE SEVERAL VIEWS OF THE DRAWINGS

FIGS. 2A and B are graphs comparing of the effects of various analogs of 20-HETE on the diameter of isolated renal interlobular arteries.

FIGS. 4A and B are graphs of antagonist activity of other analogs on the vasocnostrictor response to 20-HETE in isolated renal interlobular arteries.

FIG. 5 is a schematic of the structures of specific 20-HETE agonists and antagonists described herein.

FIG. 6 is a diagram of a generalized 20-HETE agonist/antagonist and provides schemes for the synthesis of agonists and antagonists.

FIGS. 7A, B is a set of examples of suitable compounds.

DETAILED DESCRIPTION OF THE INVENTION

Figure 1:
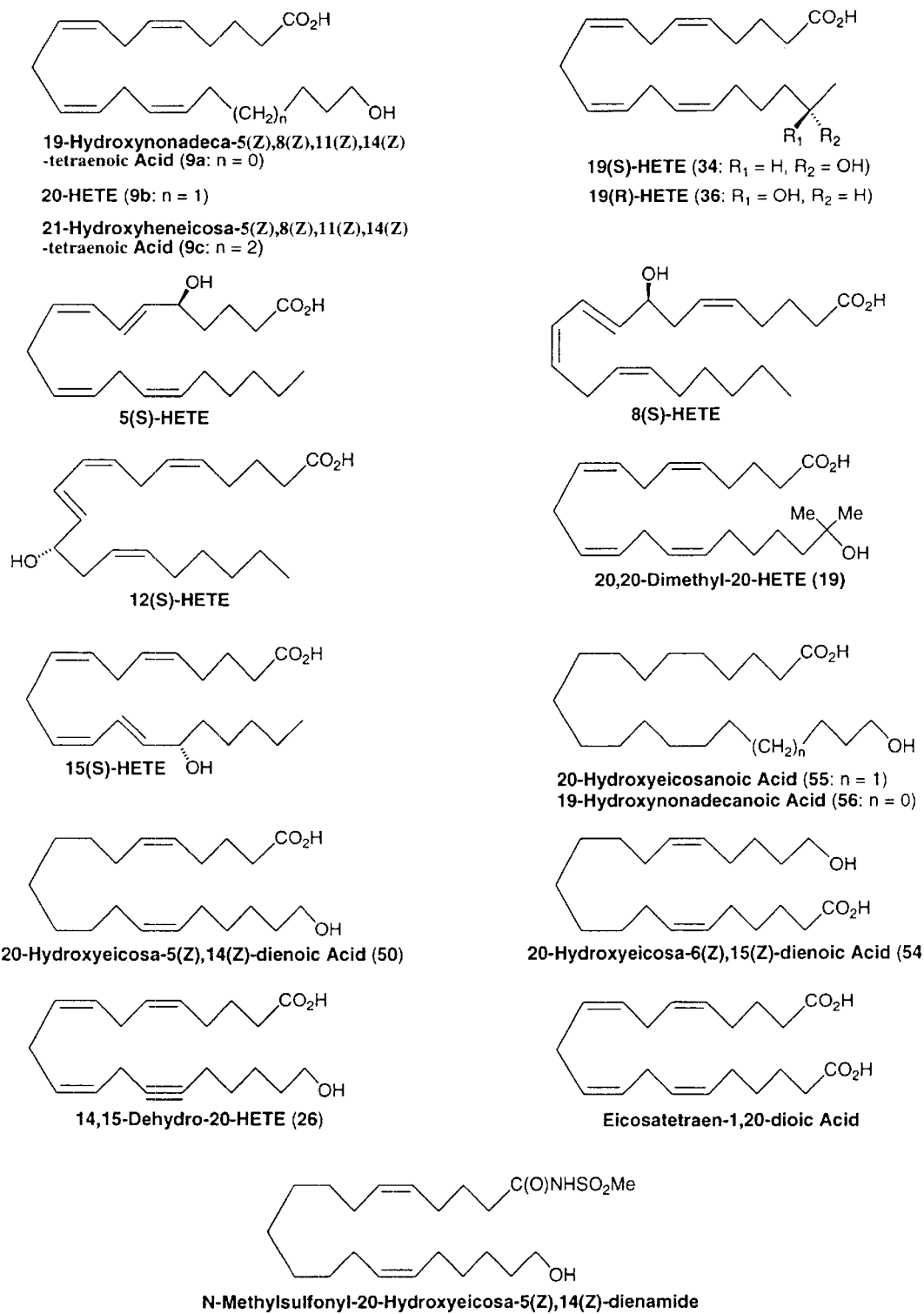
FIG. 1 is a set of structures of some of the various analogs of 20-HETE described herein.

In one embodiment, the present invention is a method of reducing a patient's vascular diameter or preventing 20-HETE from reducing vascular diameter, comprising the step of supplying to the patient an effective amount of a 20-HETE antagonist or agonist.

In a preferred embodiment of the present invention, the compound is of the following formula:

$$X \begin{matrix} sp^{<3} \text{Center}_m - W - R_1 \\ \\ sp^{<3} \text{Center}_n - Y - R_2 \end{matrix}$$

$R_1$ is preferably selected from the group consisting of carboxylic acid; phenol; amide; imide; sulfonamide; sulfonimide; active methylene; 1,3-dicarbonyl; alcohol; thiol; amine; tetrazole and other heteroaryl groups;

$R_2$ is preferably selected from the group consisting of carboxylic acid; phenol; amide; imide; sulfonamide; sulfonimide; active methylene; 1,3-dicarbonyl; alcohol; thiol; amine; tetrazole and other heteroaryl;

W is a carbon chain (preferably $C_1$ through $C_{25}$) and may be linear, cyclic, or branched. W may comprise heteroatoms, such as S, O, N, and Se or may comprise an aryl or heteroaryl moiety;

Y is a carbon chain (preferably $C_1$ through $C_{25}$) and may be linear, cyclic, or branched. Y may comprise heteroatoms such as S, O, N or Se and may comprise an aryl or heteroaryl moiety;

$sp^{<3}$ Center is preferably selected from vinyl; aryl; heteroaryl; cyclopropyl; and acetylenic groups;

X is an alkyl (and may be linear, branched, or cyclic), polycyclic; vinyl; aryl; heteroaryl; cyclopropyl; or acetylenic moiety and may comprise heteroatoms;

m is 0, 1, 2, 3, 4 or 5 and n is 0, 1, 2, 3, 4 or 5.

In all of our specific examples, the first carbon was a carboxyl group. However, this could be replaced by another type of ionizable group, as detailed in our generalized structure (FIG. 6A). The compound was an agonist if it had a pair of double bonds and hydroxyl group on the 20–21 carbon of the chain. (The overall distance between the ionizable group $C_1$ and the reactive group on $C_{20}$ or $C_{21}$ would equal that of a carbon chain of 20–21 carbons in length, but the chain could comprise other atoms, such as O, S or N.) It was an antagonist if it lacked a hydroxyl group at this location.

From these structure activity studies, we propose a general scheme for the structure of agonists and antagonists of the actions of 20-HETE illustrated in FIG. 6A. Agonists and antagonists both require a carboxyl or other ionizable group at one end of the molecule to serve as an anchor point with the putative receptor. They also require a double bond or other functional group at a distance equal to 14–15 carbons from $C_1$ (the carboxyl or ionizable group) capable of forming a n bond to stabilize the molecule in the acceptor site. An agonist will also have a hydroxyl or other ionizable or functional group capable of hydrogen bonding that interacts with the receptor at a distance equivalent to 20 or 21 carbons from the ionizable group on carbon 1. Antagonists have a similar structure, but lack a reactive group on the 20–21 carbon.

In addition, our prototype examples indicate that a hydroxyl or other functional group located on the 19-carbon of the chain enhances antagonist activity.

The Examples below characterize various analog compounds we synthesized and tested in order to evaluate the structural determinants of the vasoconstrictor response in interlobular arteries microdissected from the kidney of rats. From these studies we also discovered specific agonists and antagonists to 20-HETE.

In one embodiment, the present invention is methods of using various compounds of the above formula wherein the compounds are either agonists or antagonists of 20-HETE.

In one embodiment, the compound is an agonist and the vascular diameter is reduced. Preferably, the compound comprises a hydroxyl group 5 or 6 carbons from a double bond and is selected from the group consisting of 21-HETE, ps20-HETE and dimethyl 20-HETE.

In another embodiment, the compound is a 20-HETE antagonist and the vascular diameter is prevented from being reduced by 20-HETE. Preferably, the compound has an OH group that is not located 5 or 6 carbons from a double bond and is selected from the group consisting of 5(S)-HETE, 15(S)-HETE, 19(S)-HETE, 19-hydroxynonadeca-5(Z),8(Z),11(Z),14(Z)-tetraenoic acid and 20-hydroxyeicosa 6(Z),15(Z)-dienoic acid.

Compounds of the present invention can be created analogously to the descriptions of compound synthesis described below in the Examples.

One may most easily determine whether a compound is a 20-HETE agonist or antagonist by reference to the Examples below. A compound is a 20-HETE agonist if the compound reduces a patient's vascular diameter.

By "reducing a patient's vascular diameter" Applicants mean a reduction as described below in the methods. Applicants have described a test system of isolated vessels wherein vessels are mounted on glass micropipettes and exposed to various test compounds. We believe that a reduction of vascular diameter of at least 20% indicates that a compound is a 20-HETE agonist.

We also disclose below a test for 20-HETE antagonist activity. In this analysis, test compounds were analyzed by a cumulative dose response curve to 20-HETE generated before and after the addition of the test compound. Addition of certain antagonists, such as 5-HETE or 15-HETE, blocked the vasoconstrictor response to 20-HETE. We envision suitable antagonists as similarly blocking the vasoconstrictor response.

We propose that the agonists and antagonists of 2-HETE be used therapeutically in vivo by human patients.

It is known in the art that drugs that reduce diameter in vitro on isolated vessels also work in vivo. (Zou, A. P., *Am. J. Physiol.* 270:R226-R237, 1996; Zou, A. P., *Am. J. Physiol.* 266:F275–F282, 1994; Harder, D. R., supra, 1997; Alonso-Galicia, M., *Hypertension* 29:320–325, 1997.)

In another embodiment, the present invention is the use of 20-HETE agonists and antagonists in certain therapeutic applications. Preferably, the 20-HETE antagonists and agonists are of the formula described above.

We envision that 20-HETE antagonists may be used to moderate a patient's elevated endogenous production of 20-HETE as described below in the Examples. This modulation may be useful for a patient who has coronary artery disease, diabetes, toxemia of pregnancy (pre-eclampsia), hepatorenal syndrome, cyclosporin-induced nephrotoxicity, cerebrivaspasm stroke or hypertension.

We also envision that a 20-HETE antagonist may be useful to treat a patient with septic shock or other inflammatory disease associated with induction of the synthesis of nitric oxide as described below in the Examples.

In another embodiment we envision that a 20-HETE antagonist may prevent vascularization of granular of neoplastic tissues and be useful in the treatment of cancer as described below in the Examples.

We also envision that a 20-HETE agonist will have certain therapeutic uses as described below in the Examples. In one embodiment, the agonist may provide a diuretic effect and may be useful for a patient with congestive heart failure, pulmonary edema, hepatorenal syndrome and hypertension.

In another embodiment, the 20-HETE agonist may be useful to a patient with asthma. Preferably, the compound would be delivered as inhalational therapy as described below in the Examples.

In another embodiment, the patient may have pulmonary hypertension and 20-HETE or a 20-HETE agonist is infused to dilate the pulmonary circulation.

In another embodiment, a patient may have cerebral vascular injury, vasospasm, migraine or cluster headaches, stroke or cocaine-induced vasospasm and is treated with a 20-HETE antagonist to increase blood flow and relieve symptoms.

In another embodiment, the present invention is a pharmaceutical preparation comprising one of the following compounds and a pharmaceutically acceptable carrier:

20-hydroxyeicoanoic acid S(20-HETE), 19-hydroxynonadecanoic acid ($sC_{19}$ analog),

19S-HETE, 20,20 dimethyl-20-HETE, 20-hydroxyeicosa-5(Z),14(Z)-dienoic acid (ps 20-HETE), 20-hydroxyeicosa 6(Z),15(Z)-dienoic acid (ps rev 20-HETE), 19-hydroxy-nonadeca-5(Z),8(Z),11(Z),14(Z)-tetraenoic acid($C_{19}$ analog), 21-hydroxyheneicosa-5(Z),8(Z),11(Z),14(Z)-tetraenoic acid (21-HETE), N-methylsulfonyl-20-hydroxyeicosa-5(Z),14(Z)-dienamide, and N-methylsulfonyl-20-hydroxyeicosa-6(Z),15(Z)-dienoic acid.

EXAMPLES

In General

Recent studies have indicated that arachidonic acid (AA) is primarily metabolized by a P4504A dependent pathway to 20-hydoxyeicosatetraenoic acid (20-HETE) in the kidney and in the peripheral vasculature and that 20-HETE serves as a critical second messenger in the regulation of renal and peripheral vascular tone, renal function and the long-term control of arterial pressure. In this regard, 20-HETE is a potent vasoconstrictor that inhibits the opening of $Ca^{++}$-activated $K^+$ channels in vascular smooth muscle cells. It promotes $Ca^{2+}$ entry by depolarizing VSM cells secondary to blockade of $K_{Ca}$ channels and by increasing the conductance of L-type $Ca^{2+}$ channels (Harder, D. R., supra, 1997; Roman, R. J., supra, 1999). Inhibitors of the formation of 20-HETE block the myogenic response of renal, cerebral and peripheral arterioles to elevations in transmural pressure and autoregulation of renal and cerebral blood flow in vivo (Harder, D. R., et al., supra, 1997; Zou, A., et al., supra, 1996; Zou, A. P., et al., supra, 1994). They also attenuate the vasoconstrictor response endothelin, AII and inhibitors of NO synthase (Oyekan, A. O., *Am. J. Physiol.* 274:R52-R61, 1998; Sun, D.-W., et al., *Circ. Res.* 83:1069–1079, 1998), the vasoconstrictor response to elevations in tissue $PO_2$, (Harder, D. R., *Circ. Res.* 79:54–61, 1996; Lombard, J. H., *Am. J. Physiol.* 276:H503-H507, 1999), the mitogenic actions of growth factors in vascular smooth muscle and renal mesangial cells (Lin, et al., *Am. J. Physiol.* 269:F806–F816, 1995; Uddin, et al., *Hypertension* 31:242–247, 1998), and the development of hypertension in spontaneously hypertensive rats and other experimental models of hypertension (Roman, et al., *Am. J. Hypertension* 10:638–678, 1997).

In the kidney, 20-HETE is also produced by renal tubular cells where it participates in the regulation of sodium transport in the proximal tubule and thick ascending limb of the loop of Henle. (Roman R. S., supra, 1999), 20-HETE is also produced by the airways in human and rabbit lungs where is serves as an potent endogenously produced bronchodilator. (Zhu, et al., supra, 1998; Jacobs, et al., supra, 1999).

Despite the importance of 20-HETE in the regulation of renal function, vascular tone, and airway resistance, little is known its mechanism of action. Recent studies have indicated that the mitogenic actions of 20-HETE and its effects on vascular tone and sodium transport are associated with activation of PKC and MAP kinase signal transduction cascades. (Sun, C. W., et al., supra, 1999). activation of these pathways are usually triggered by receptor mediated events. However, at present time there is no previously published evidence for a 20-HETE receptor. There have been no previous studies to determine whether 20-HETE binds to membrane proteins or whether the vasoconstrictor properties of 20-HETE can be mimicked by other analogs.

Thus, the purpose of the present study was to perform structure activity studies with a series of synthetic 20-HETE analogs to evaluate the structural determinants of the vasoconstrictor response in interlobular arteries microdissected from the kidney of rats.

Methods

General. Experiments were performed on 10 to 12-week old male Sprague-Dawley rats purchased from Harlan Sprague-Dawley Laboratories (Indianapolis, Ind.). The rats were housed in the animal care facility at the Medical College of Wisconsin, which is approved by the American Association for the Accreditation of Laboratory Animal Care. The animals had free access to food and water. All protocols involving animals received approval by the Animal Care Committee of the Medical College of Wisconsin.

Isolated vessel studies. Interlobular arterioles (70–120 $\mu$m inner diameter) were microdissected from the kidneys of rats. The vessels were mounted on glass micropipettes in a perfusion chamber containing physiological saline solution equilibrated with a 95% $O_2$ —5% $CO_2$ gas mixture and maintained at 37° C. The vessel were secured to the pipettes and side branches were tied off with 10–0 silk suture. The inflow pipette was connected to a pressurized reservoir to control of intraluminal perfusion pressure, which was monitored using a transducer (Cobe, Lakewood, Colo.). The vessels were stretched to in vivo length measured before microdissection. The outflow cannula was clamped off and intraluminal pressure was maintained at 90 mm Hg during the experiment. Vascular diameters were measured with a video system composed of a stereo microscope (Carl Zeiss, Inc., Germany), a CCTV television camera (KP-130AU, Hitachi, Japan), a videocassette recorder (AG-7300, Panasonic, Japan), a television monitor (CVM-1271, Sony, Japan), and a video measuring system (VIA-100, Boeckeler Instrument Co., Tucson, Ariz.).

The composition of the perfusate and the bath was (in mM): 119 NaCl, 4.7 KCl, 1.17 $MgSO_4$, 1.6 $CaCl_2$, 12 $NaHCO_3$, 1.18 $NaH_2PO_4$, 0.03 EDTA and 10 glucose, pH 7.4. Indomethacin (5 $\mu$M), baicalein (0.5 $\mu$M) and 17-ODYA (1 $\mu$M) were added to the bath to block the endogenous formation and metabolism of eicosanoids via the cyclooxygenase, lipoxygenase and cytochrome P450 pathways. After the equilibration period, cumulative dose response curves were generated for each of the 20-HETE analogs.

Effect of the position of the hydroxyl group on the vasoconstrictor response to 20-HETE. These experiments examined the effects of increasing concentrations of 5(S)-, 8(S)-, 12(S)-, 15(S)-, and 19(S)-HETE on the diameter of isolated, pressured rat renal interlobular arteries. All of these analogs have the same number of carbons, double bonds and molecular weight as 20-HETE (FIG. 1). The major difference between these compounds and 20-HETE is the position of the OH group along the carbon chain. Additional experiments were performed with arachidonic acid and 20-carboxyarachidonic acid, which are structurally similar to 20-HETE but lack a hydroxyl group on the $20^{th}$ carbon and 20-hydroxyeicosa-6, 15-dienoic acid (reverse 20-HETE) which has the carboxy- and hydroxy-moieties on the $1^{st}$ and $20^{th}$ carbons reversed. Cumulative dose response curves were generated for each compound ($10^{-8}$ to $10^{-6}$ M) in the presence of indomethacin, baicalein, and 17-ODYA. Vascular diameters were recorded 2 to 3 minutes after the addition of the compounds to the bath.

Effect of the double bonds and carbon chain length to the vasoconstrictor response to 20-HETE. We next examined the importance of the double bonds and the length of the carbon chain to the vasoconstrictor response to 20-HETE. In these studies, the double bonds in the 20-HETE molecule were removed creating partial and saturated 20-HETE derivatives (20-hydroxyeicosa-6(Z),15(Z) dienoic acid; 20-hydroxyeicosanoic acid, FIG. 1). 20-HETE was also shortened by one carbon, creating a 19-carbon analog (19-hydroxynonadeca-5(Z),8(Z),11(Z),14(Z)-tetraenoic acid, FIG. 1) and double bonds were removed, creating a saturated 19-carbon analog (19 hydroxynonadecanoic acid, FIG. 1). In addition, one carbon was added to the 20-HETE molecule, creating a 21-carbon analog (21-hydroxyheneicosa-5(Z),8(Z),11(Z),14(Z)-tetraenoic acid, FIG. 1), and finally the hydrogen atoms on the $20^{th}$ carbon were replaced with methyl groups (20,20-dimethyl-20-HETE). After the equilibration period, cumulative dose response curves to these analogs ($10^{-8}$ to $10^{-6}$ M) were generated in the presence of indomethacin, baicalein, and 17-ODYA. Vascular diameter was recorded 2 to 3 minutes after addition of these compounds to the bath.

20-HETE antagonist activity. The inactive analogs of 20-HETE were further tested for antagonist activity. In these experiments, cumulative dose response curves to 20-HETE ($10^{-8}$ to $10^{-6}$ M) were generated before and after addition of 5(S)-HETE (0.5 $\mu$M), 8(S)-HETE (1 $\mu$M), 12(S)-HETE (0.5 $\mu$M), 15(S)-HETE (1 $\mu$M), 19(S)-HETE (1 $\mu$M), the $C_{19}$-analog (1 $\mu$M), arachidonic acid (1 $\mu$M), 20-carboxy-arachidonic acid (1 $\mu$M), reverse 20-HETE (1 $\mu$M), saturated 20-HETE (1 $\mu$M), and the saturated $C_{19}$-analog (1 $\mu$M) to the bath. Vascular diameters were recorded 2 to 3 minutes after the addition of each dose of 20-HETE to the bath.

Drugs and chemicals. All chemicals were of analytical grade. Indomethacin was obtained from Sigma Chemicals (St. Louis, Mo.). 5(S)-, 8(S)-, 12(S), 15(S), and 19(S)-HETE, baicalein and 17-ODYA were purchased from Biomol Corp. (Plymouth Meeting, Pa.). 20-HETE, reverse 20-HETE, the 19-carbon analog, dimethyl 20-HETE, 21-HETE, 20-carboxyarachidonic acid, and the saturated and partially saturated $C_{19}$ and 20-HETE analogs, were all synthesized as described below.

Chemical Syntheses of 20-HETE and Analogs

Figure 8A:
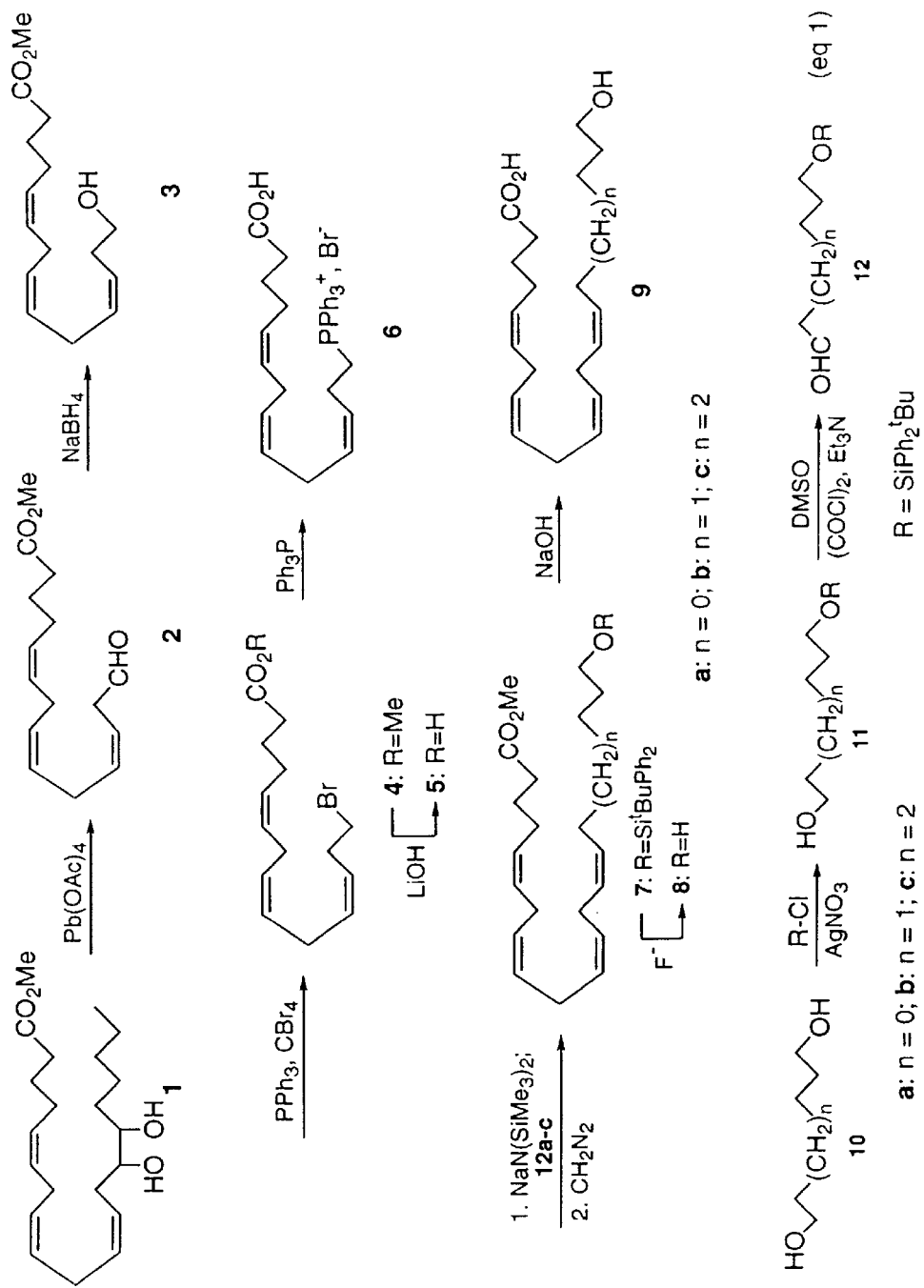
FIGS. 8A, B, C, D, E and F is a set of schemes for the synthesis of 20-HETE agonists and antagonists.

The preparations below refer to FIGS. 1, 8A, B, C, D, E and F.

Preparation of 20-HETE (9b): To a vigorously stirring, −40° C. solution of methyl 14,15-dihydroxyeicosatrienoate (1) (700 mg, 1.98 mmol) in anhydrous $CH_2Cl_2$ (30 mL) was added Pb $(OAc)_4$ (890 mg, 2.00 mmol) portionwise over 2 minutes (Scheme 1; FIG. 8A). After 30 minutes, the reaction mixture was passed through a pad of silica gel to remove inorganic salts. The filter cake was washed with EtOAc/hexane (1:1, 30 mL) and the combined filtrates were evaporated in vacuo to give aldehyde 2 (435 mg, 87%) as a labile, colorless oil that was used immediately in the next step. $^1$H NMR (250 MHz, $CDCl_3$): δ 1.60–1.78 (m, 2H), 2.00–2.15 (m, 2H), 2.30 (t, J~7.4 Hz, 2H), 2.70–2.85 (m, 4H), 3.18–3.28 (m, 2H), 3.65 (s, 3H), 5.28–5.75 (m, 6H), 9.65 (t, J~1.8 Hz, 1H); TLC: EtOAc/hexane (1:1), $R_f$~0.5.

Sodium borohydride (139 mg, 3.65 mmol) was added portionwise to a stirring solution of crude 2 (435 mg, 1.76 mmol) in MeOH/$CH_2Cl_2$ (1:2, 10 mL). After 45 minutes, the mixture was concentrated under reduced pressure and the residue was purified by $SiO_2$ column chromatography using EtOAc/hexanes (2:3) to furnish alcohol 3 (350 mg, 80%) as a colorless oil. $^1$H NMR (250 MHz, $CDCl_3$): δ 1.60–1.75 (m, 2H), 2.04–2.15 (m, 2H), 2.25–2.38 (m, 4H), 2.72–2.85 (m, 4H), 3.65 (t, J~7.2 Hz, 2H), 3.68 (s, 3H), 5.28–5.60 (m, 6H); TLC: EtOAc/hexanes (1:1), $R_f$~0.39.

Triphenylphosphine (495 mg, 1.89 mmol) was added portionwise to a stirring, 0° C. solution of 3 (340 mg, 1.35 mmol) and carbon tetrabromide (585 mg, 1.75 mmol) in dry $CH_2Cl_2$ (15 mL). After 40 minutes, the solvent was removed in vacuo and the residue was purified by $SiO_2$ column chromatography using $CH_2Cl_2$ as eluent to yield bromide 4 (375 mg, 88%) as a mobile, colorless oil. $^1$H NMR (250 MHz, $CDCl_3$): δ 1.64–1.75 (m, 2H), 2.04–2.15 (m, 2H), 2.25–2.36 (m, 2H), 2.60–2.70 (m. 2H), 2.75–2.84 (m, 4H), 3.38 (t, J~7.2 Hz, 2H), 3.65 (s, 3H), 5.30–5.60 (m, 6H); TLC: EtOAc/hexane (1:1) $R_f$~0.61.

Aqueous LiOH (2 mL of 1 M soln) was added dropwise to a 0° C. solution of 4 (375 mg, 1.19 mmol) in tetrahydrofuran (THF)/$H_2O$ (5:1, 20 mL). After stirring at ambient temperature for 12 hours, the pH was adjusted to 4.5 using 1 M aqueous oxalic acid and the THF was evaporated under reduced pressure. The residue was diluted with $H_2O$ (15 mL) and extracted with EtOAc (3×10 mL). The combined organic extracts were washed with $H_2O$ (15 mL), dried over $Na_2SO_4$, and evaporated to give bromo-acid 5 (318 mg, 89%) as a colorless oil. $^1$H NMR (250 MHz, $CDCl_3$): δ 1.63–1.76 (m, 2H), 2.08–2.16 (m, 2H), 2.40 (t, J~7.1 Hz, 2H), 2.60–2.70 (m, 2H), 2.75–2.86 (m, 4H), 3.40 (t, J~7.2 Hz, 2H), 5.30–5.55 (m, 6H); TLC: EtOAc/hexanes (3:1), $R_f$~0.34.

A mixture of triphenylphosphine (524 mg, 2 mmol, 3.5 equiv.) and bromo-acid 5 (305 mg, 1 mmol) in dry $CH_3CN$ (6 mL) was heated at 85° C. in a sealed tube for 60 hours. Solvent evaporation and $SiO_2$ chromatographic purification using MeOH/$CH_2Cl_2$ (5:95) afforded phosphonium salt 6 (530 mg, 92%) as a viscous, hygroscopic oil. $^1$H NMR (250 MHz, $CDCl_3$): δ 1.55–1.70 (m, 2H), 1.96–2.10 (m, 2H), 2.40 (t, J~7.1 Hz, 2H), 2.42–2.60 (m, 2H), 2.62–2.70 (m, 4H), 3.75–3.88 (m, 2H), 5.20–5.50 (m, 6H), 7.65–7.80 (m, 15H); TLC: MeOH/$CH_2Cl_2$ (1:7), $R_f$~0.21.

Lithium bis(trimethylsilyl)amide (0.32 mL of a 1 M solution in THF) was added dropwise to a −78° C. solution of 6 (90 mg, 0.16 mmol) in THF/hexamethylphosphoramide (HMPA) (4:1, 2.5 mL). The mixture gradually developed the dark yellow coloration characteristic of ylides. The reaction mixture was kept at −40° C. for 1 hour, re-cooled to −78° C. and a solution of aldehyde 12b (30 mg, 0.133 mmol) in anhydrous THF (1 mL) was added dropwise. Following an additional 1.5 hours, the reaction was quenched with 50% aqueous $NH_4OAc$, extracted with EtOAc (3×10 mL), and the combined organic extracts were washed with $H_2O$ (2×5 mL), brine (5 mL), dried over $Na_2SO_4$, and the solvent was evaporated in vacuo. The residue was redissolved in MeOH/$Et_2O$ (1:5, 4 mL) and treated with excess ethereal diazomethane at 0° C. for 0.5 hours. Removal of all volatiles and $SiO_2$ chromatographic purification of the resultant oil using EtOAc/hexanes (1:10) furnished a mixture of silyl-ester 7b and $\Delta^{14,15}$-trans-7b (8:1, 73%) that was more conveniently resolved after the next step. $^1$H NMR of 7b/$\Delta^{14,15}$-trans-7b mixture (250 MHz, $CDCl_3$): δ 0.84 (s, 9H), 1.20–1.75 (m, 8H), 2.00–2.18 (m, 4H), 2.30 (t, J~7.5 Hz, 2H), 2.72–2.85 (m, 6H), 3.60 (t, J~7.3 Hz, 2H), 3.65 (s, 3H), 5.30–5.40 (m, 8H), 7.38–7.45 (m, 6H), 7.59–7.68 (m, 4H); TLC: EtOAc/hexanes (1:2), $R_f$0.62.

A solution of 7b/$\Delta^{14,15}$-trans-7b (63 mg, 0.11 mmol) and n-tetrabutylammonium fluoride (0.22 mmol, 5 equiv.) in THF (8 mL) was maintained at room temperature for 3 hours. The solvent was evaporated and the residue was dissolved in EtOAc (10 mL), then washed with $H_2O$ (2×5 mL), brine (8 mL), dried over $Na_2SO_4$, and concentrated in vacuo. Column chromatography ($SiO_2$) of the residue using $Et_2O$/hexanes (7:3) gave a mixture of ester 8b and its $\Delta^{14,15}$-trans-isomer (77%) as a colorless oil which was resolved by HPLC on a Varian Microsorb Si 5μ (10×250 mm) column eluted isocratically with hexane/EtOH (99.4:0.6) at 6 mL/min. and monitored at 205 nm (8b: $R_t$~32.4 min.; $\Delta^{14,15}$-trans-8b: $R_t$~34.8 min). $^1$H NMR (250 MHz, $CDCl_3$): δ 1.25–1.75 (m, 8H), 2.00–2.20 (m, 5H), 2.30 (t, J~7.5 Hz, 2H), 2.72–2.85 (m, 6H), 3.65 (t, J~7.3 Hz, 2 H), 3.70 (s, 3H), 5.30–5.50 (m, 8H).

Aqueous NaOH (0.149 mL of a 1 M soln, 0.149 mmol) was added to a 0° C. solution of 8b (12.4 mg, 0.037 mmol) in THF/$H_2O$ (3:1, 2 mL). After stirring at ambient temperature overnight, the reaction mixture was diluted with $H_2O$ (3 mL), adjusted to pH 6.5 by dropwise addition of 1 M aqueous oxalic acid, then extracted with EtOAc (3×3 mL). The combined organic extracts were washed with $H_2O$ (10 mL), dried over $Na_2SO_4$, and evaporated to give 20-HETE (9b) (8.5 mg, 72%) as a colorless oil identical in all respects to an authentic sample. $^1$HPLC: Phenomenex Nucleosil 5μ $C_{18}$ (4.6×250 mm) column eluted linearly from $CH_3CN$/$H_2O$/HOAc (49.95:49.95:0.1) to $CH_3CN$/HOAc (99.9:0.1) over 40 minutes at 1 mL/min. and monitored at 205 nm ($R_t$~18 min.). TLC: MeOH/$CH_2Cl_2$ (1:10), $R_f$~0.45.

Preparation of Aldehyde 12b: tert-Butylchlorodiphenylsilane (400 mg, 1.45 mmol) and $AgNO_3$ (250 mg, 1.47 mmol) were added to a solution of 1,6-hexanediol (10b) (343 mg, 2.90 mmol) in THF/pyridine (15:1, 32 mL) (eq. 1). After stirring in the dark for 12 hours, the reaction mixture was filtered through a bed of CELITE and the filter cake was washed with THF (10 mL). The combined filtrates were evaporated and the residue was purified by $SiO_2$ column chromatography using MeOH/$CH_2Cl_2$ (1:49) to give 11b (495 mg, 96% based on silylating agent). $^1$H NMR (250 MHz, $CDCl_3$): δ 1.04 (s, 9H), 1.16–1.70 (m, 8H), 3.48–3.76 (m, 4H), 7.38–7.44 (m, 6H), 7.61–7.66 (m, 4H); TLC: MeOH/$CH_2Cl_2$ (5:95), $R_f$~0.49.

Freshly distilled oxalyl chloride (353 mg, 2.78 mmol) was added to a −78° C. solution of methyl sulfoxide (DMSO) (543 mg, 6.95 mmol) in anhydrous $CH_2Cl_2$ (5 mL). After 10 minutes, silyl ether 11b (495 mg, 1.39 mmol) in $CH_2Cl_2$ (3 mL) was added dropwise and the mixture was stirred for an additional 1.5 hours. Triethylamine (702 mg, 6.95 mmol) was added and the mixture was warmed to −20° C. over 30 minutes, then poured into saturated aqueous $NaHCO_3$ and the layers were separated. The aqueous layer was further extracted with $CH_2Cl_2$ (2×10 mL). The combined organic extracts were washed with brine (15 mL), dried over $Na_2SO_4$, evaporated, and the residue was purified by $SiO_2$ column chromatography using $CH_2Cl_2$ to give aldehyde 12b (450 mg, 92%). $^1$H NMR (250 MHz, $CDCl_3$) δ 1.04 (s, 9H), 1.36–1.80 (m, 8H), 2.24–2.52 (m, 2H), 3.64 (t, J~6 Hz, 2H), 7.32–7.44 (m, 6H), 7.63–7.70 (m, 4H), 9.72 (t, J~1.8 Hz, 1H); TLC: $MeOH/CH_2Cl_2$ (1:49), $R_f$~0.71.

Preparation of 19-Hydroxynonadeca-5(Z),8(Z),11(Z),14(Z)-tetraenoic Acid (9a) and 21-Hydroxyheneicosa-5(Z),8(Z),11(Z),14(Z)-tetraenoic Acid (9c): $C_{19}$-Homolog 9a and $C_{21}$-homolog 9c were prepared in the same manner and in comparable yields as described for 9b (Scheme 1) using Wittig salt 6 and aldehydes 12a and 12c (eq 1), respectively. The TLC characteristics and NMR spectra of 9a and 9c, except for integration, were virtually identical with 9b.

Figure 8B:
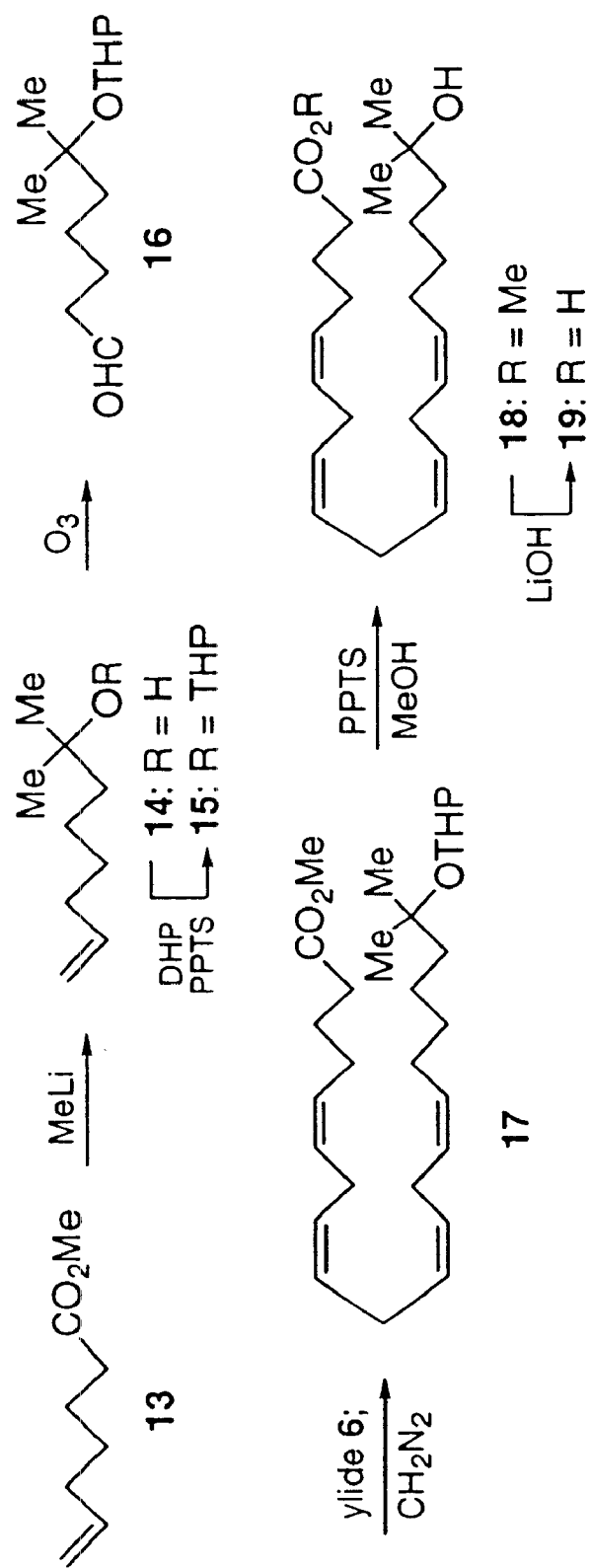
Figure 8C:
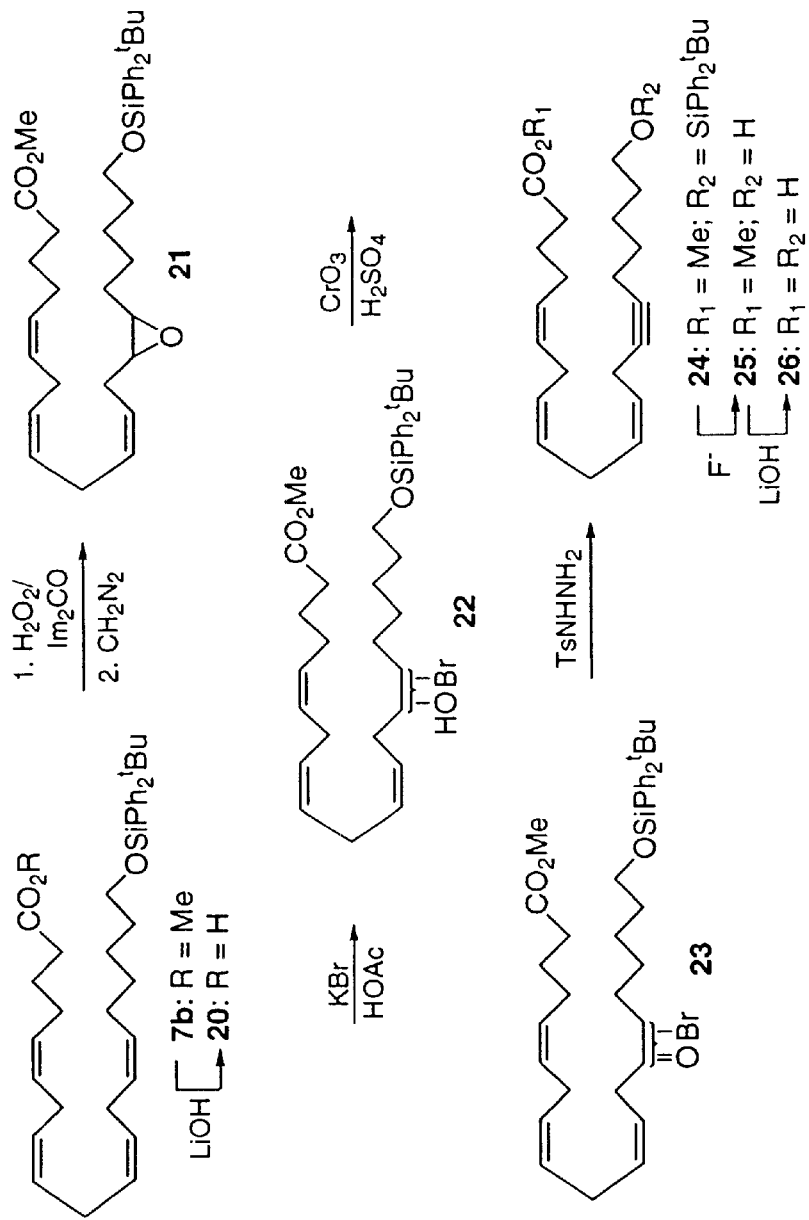

Preparation of 20,20-Dimethyl-20-HETE (19): MeLi (1.4 M solution in $Et_2O$, 10.4 mL, 14.6 mmol) was added dropwise to a stirring, room temperature solution of methyl 6-heptenoate (13) (946 mg, 6.65 mmol) in anhydrous $Et_2O$ (30 mL) under argon (Scheme 2; FIG. 8B). After 12 hours, the reaction mixture was adjusted to pH 4 by the addition of 5% hydrochloric acid and extracted with EtOAc (3×10 mL). The combined organic extracts were dried over $Na_2SO_4$ and all volatiles were removed in vacuo to afford alcohol 14 (950 mg, 100%) sufficiently pure to be used directly in the next step. $^1$H NMR ($CDCl_3$, 250 MHz): δ 1.22 (s, 6H), 1.26–1.46 (m, 6H), 2.03–2.18 (m, 2H), 4.92–5.08(m, 2H), 5.72–5.90 (m, 1H); TLC: EtOAc/hexanes (1:4), $R_f$~0.38.

A mixture of alcohol 14 (870 mg, 6.1 mmol), 3,4-dihydro-2H-pyran (DHP) (1.12 mL, 12.2 mmol), and pyridinium p-toluenesulfonate (PPTS) (153 mg, 0.61 mmol) in $CH_2Cl_2$ (43 mL) was stirred at ambient temperature for 12 hours, then diluted with $Et_2O$ (50 mL) and filtered. The filtrate was evaporated in vacuo and the residue was chromatographed on $SiO_2$ using EtOAc/hexanes (5:95) to afford THP ether 15 (1.13 g, 82%) as a colorless oil. 1H NMR (250 MHz, $CDCl_3$): δ 1.19 (s, 3H), 1.21 (s, 3H), 1.30–1.42 (m, 4H), 1.42–1.58 (m, 6H), 1.60–1.68 (m, 1H), 1.75–1.90 (m, 1H), 2.01–2.12 (m, 2H), 3.38–3.44 (m, 1H), 3.90–3.99 (m, 1H), 4.67–4.70 (m, 1H), 4.92–5.08 (m, 2H), 5.72–5.90 (m, 1H); TLC: EtOAc/hexanes (15:85), $R_f$~0.64.

A 0° C. solution of THP ether 15 (565 mg, 2.5 mmol) in $CH_2Cl_2$ (10 mL) was saturated with a continuous stream of $O_3$ for 10 minutes. After purging with argon to remove excess $O_3$, neat $Me_2S$ (1 mL) was added and the mixture was stirred at room temperature for 2 hours. Evaporation of all volatiles in vacuo and chromatographic purification of the residue on $SiO_2$ using EtOAc/hexane (15:85) as eluent yielded aldehyde 16 (390 mg, 65%) as a colorless oil. $^1$H NMR ($CDCl_3$, 250 MHz): δ 1.18 (s, 3H), 1.21 (s, 3H), 1.40–1.80 (m, 12H), 2.43 (dt, J~1.5 and 6.4 Hz, 2H), 3.40–3.52 (m, 1H), 3.90–4.00 (m, 1H), 4.68–4.74 (m, 1H), 9.78 (t, J~1.5 Hz, 1H); TLC: EtOAc/hexanes (1:9), $R_f$~0.19.

Lithium bis(trimethylsily)amide (0.3 mL of a 1 M soln, 0.30 mmol) was added slowly to a −78° C. suspension of phosphonium salt 6 (82 mg, 0.15 mmol) in THF/HMPA (4:1, 5 mL) under argon. The reaction mixture was stirred at −78° C. for another 30 minutes, warmed to −40° C. for 1 hour, then re-cooled to −78° C. Aldehyde 16 (43 mg, 0.19 mmol) in THF (1.5 mL) was added dropwise to the above yellow ylide solution at −78° C. After 1.2 hours, the reaction was quenched with 50% aqueous $NH_4OAc$ solution and extracted with EtOAc (3×20 mL). The combined organic extracts were washed with $H_2O$ (5 mL), brine (5 mL), dried over $Na_2SO_4$, and evaporated in vacuo. The residue was dissolved in $Et_2O$ and treated with excess ethereal $CH_2N_2$ for 15 minutes. Evaporation of all volatiles in vacuo and purification of the residue via PTLC [$SiO_2$: $Et_2O$/hexanes (7:3), $R_f$~0.56] gave THP-ester 17 (35 mg, 53%) as a colorless oil. $^1$H NMR (250 MHz, $CDCl_3$): δ 1.20 (s, 3H), 1.23 (s, 3H), 1.23–1.85 (m, 12H), 1.95–2.20 (m, 4H), 2.34 (t, J~7.6 Hz, 2H), 2.70–2.90 (m, 6H), 3.35–3.50 (m, 1H), 3.68 (s, 3H), 3.85–4.00 (m, 1H) 4.68–4.74 (m, 1H), 5.20–5.45 (m, 8H).

A mixture of THP-ester 17 (35 mg, 0.08 mmol) and PPTS (2 mg) in MeOH (1 mL) was stirred at room temperature for 1 hour. Evaporation of the solvent in vacuo and purification of the residue via PTLC [$SiO_2$: $Et_2O$/hexane (7:3), $R_f$~0.38] afforded hydroxy-ester 18 (23 mg, 80%) as a colorless oil. $^1$H NMR ($CDCl_3$, 250 MHz) δ 1.23 (s, 6H), 1.31–1.52 (m, 6H), 1.71 (quintet, J~7.2 Hz, 2H), 2.02–2.20 (m, 4H), 2.35 (t, J~7.4 Hz, 2H), 2.74–2.90 (m, 6H), 3.67 (s, 3H), 5.25–5.46 (m, 8H).

A mixture of ester 18 (11 mg, 0.03 mmol) and aqueous LiOH (0.17 mL of a 1 M soln, 0.17 mmol) in THF/$H_2O$ (4:1, 2.5 mL) was stirred at room temperature for 12 hours. The pH of the reaction was adjusted to 4 by addition 1 M aqueous oxalic acid and the acidified solution was extracted with EtOAc (3×5 mL). The combined organic extracts were washed with $H_2O$ (10 mL), brine (10 mL), and evaporated in vacuo to furnish acid 20,20-Dimethyl-20-HETE (19) (9.8 mg, 93%) as a colorless oil. $^1$H NMR ($CDCl_3$, 250 MHz): δ 1.21 (s, 6H), 1.30–1.52 (m, 6H), 1.71 (quintet, J~7.3 Hz, 2H), 2.03–2.20 (m, 4H), 2.33 (t, J~7.6 Hz, 2H), 2.72–2.87 (m, 6H), 5.25–5.45 (m, 8H).

Preparation of 14,15-Dehydro-20-HETE (26): A mixture of ester 7b (1.0 g, 1.74 mmol) and LiOH (9 mL of a 1 M soln, 9 mmol) in THF/$H_2O$ (4:1, 20 mL) was stirred at room temperature for 12 hours, then the organic solvent was evaporated in vacuo (Scheme 3; FIG. 8B). The residue was diluted with $H_2O$ (10 mL), acidified to pH 5.5 with 1 M oxalic acid, and extracted with EtOAc (3×50 mL). The combined organic extracts were washed with $H_2O$ (50 mL), brine (50 mL), dried over $Na_2SO_4$, and evaporated in vacuo to give acid 20 (960 mg, 98%) as a colorless oil. $^1$H NMR ($CDCl_3$, 250 MHz): δ 1.03 (s, 9H), 1.20–1.42 (m, 4H), 1.44–1.60 (m, 2H), 1.67 (quintet, J~7.1 Hz, 2H), 1.92–2.18 (m, 4H), 2.34 (t, J~7.2 Hz, 2H), 2.68–2.88 (m, 6H), 3.63 (t, J~7.4 Hz, 2H), 5.25–5.46 (m, 8H), 7.28–7.47 (m, 6H), 7.55–7.70 (m, 4H); TLC: $SiO_2$, EtOAc/hexanes (1:4), $R_f$~0.15.

A mixture of acid 20 (960 mg, 1.72 mmol) and 1,1′carbonyldiimidazole ($Im_2CO$) (418 mg, 2.58 mmol) in dry $CH_2Cl_2$ (35 mL) was stirred for 40 minutes at room temperature, then transferred via canula to a stirring, 0° C. ethereal 3.5 M $H_2O_2$ solution (20 mL, 69 mmol) containing a catalytic amount of lithium imidazole. After 5 minutes, the reaction mixture was diluted with $CH_2Cl_2$ (25 mL), powdered $KH_2PO_4$ (1.4 9, 10.32 mmol) was added, and the stirring was continued at 0° C. for an additional 5 minutes. The resultant suspension was filtered through a cotton plug into an argon flushed flask containing a suspension of anhydrous $Na_2SO_4$ (3 9) in $CH_2Cl_2$ (30 mL). The reaction mixture was stored at room temperature under an argon atmosphere for 12 hours, filtered and washed with brine (40 mL) until the aqueous layer tested negative with starch-$I_2$ paper for hydrogen peroxide. The organic layer was evaporated in vacuo and the residue was dissolved in $Et_2O$/MeOH (3:1, 15 mL) to which excess ethereal $CH_2N_2$ was added slowly at 0° C. until the yellow coloration persisted for 15 minutes. Removal of the solvent in vacuo and chromatographic purification of the residue on a $SiO_2$ column afforded epoxide 21 (650 mg, 65%) as a colorless oil accompanied by recovered 7b (200 mg). $^1$H NMR ($CDCl_3$, 250 MHz): δ 1.05 (s, 9H), 1.29–1.65 (m, 8H), 1.73 (quintet, J~7.2 Hz, 2H), 2.12 (dt, J~6.3 and 12.5 Hz, 2H), 2.18–2.47 (m, 2H), 2.34 (t, J~7.4 Hz, 2H), 2.67–3.00 (m, 6H), 3.64 (s, 3H), 3.66 (t, J~7.1 Hz, 2H), 5.28–5.58 (m, 6H), 7.30–7.50 (m, 6H), 7.60–7.74 (m, 4H); TLC: $SiO_2$, EtOAc/hexane (1:4), $R_f$~0.39.

A solution of epoxide 21 (650 mg, 1.1 mmol) in peroxide-free THF (5 mL) was added dropwise to a stirring, 0° C. mixture of AcOH/THF/saturated aq. KBr (20:4:3, 27 mL) under argon. After 10 hours, the reaction mixture was reduced in vacuo to one-quarter volume, diluted with $H_2O$ (10 mL) and extracted thrice with $Et_2O$. The combined ethereal extracts were washed with 10% aqueous $NaHCO_3$ solution, $H_2O$, brine, dried over $Na_2SO_4$, and evaporated to dryness in vacuo. Passage of the residue through a short $SiO_2$ column furnished. bromohydrin 22 (700 mg, 94%) as an inseparable mixture of regioisomers. $^1$H NMR ($CDCl_3$, 250 MHz): δ 1.05 (s, 9H), 1.16–1.48 (m, 4H), 1.49–1.64 (m, 2H), 1.71 (quintet, J~7.3 Hz, 2H), 1.80–2.07 (m, 2H), 2.13 (dt, J~6.5 and 13.3 Hz, 2H), 2.35 (t, J~7.3 Hz, 2H), 2.42 (t, J~6.5 Hz, 1H, $D_2O$ exchangeable) 2.66–2.95 (m, 4H), 3.41–3.57 (m, 1H), 3.64 (t, J~7.2 Hz, 2H), 3.65 (s, 3H), 4.00–4.15 (m, 1H), 5.27–5.61 (m, 6H), 7.27 (m, 6H), 7.59–7.70 (m, 4H); TLC: $SiO_2$, EtOAc/hexanes (1:4), $R_f$~0.39.

A solution of bromohydrin 22 (700 mg, 1.05 mmol) in acetone (4 mL) was added dropwise to a −20° C. solution of Jones reagent (0.7 mL of a 2 M soln, 1.57 mmol) in acetone (15 mL). The reaction was quenched after 30 minutes by the slow addition of excess i-PrOH, filtered to remove chromium salts, and the filtrate was evaporated in vacuo. The residue was partitioned between $H_2O$ (10 mL) and $Et_2O$ (8 mL). The layers were separated and the aqueous fraction was extracted twice more with $Et_2O$. The combined ethereal extracts were washed with brine (10 mL), dried over $Na_2SO_4$, and evaporated in vacuo. Purification of the residue on a $SiO_2$ column produced bromo-ketone 23 (500 mg, 72%) as a cclorless oil that was immediately used in the next step. $^1$H NMR ($CDCl_3$, 250 MHz): δ 1.07 (s, 9H), 1.20–1.80 (m, 8H), 2.02–2.17 (m, 2H), 2.34 (t, J~7.4 Hz, 2H), 2.64–2.91 (m, 4H), 3.40–3.54 (m, 2H), 3.64 (s, 3H), 3.66 (t, , J~6.1 Hz, 2H), 4.17–4.85 (m, 1H), 5.25–5.70 (m, 6H), 7.30–7.48 (m, 6H), 7.60–7.78 (m, 4H); TLC: $SiO_2$, EtOAc/hexane (1:4), $R_f$~0.46.

A mixture of bromo-ketone 23 (400 mg, 0.599 mmol), tosylhydrazine (224 mg, 1.199 mmol), and hydroquinone (7 mg, 0.06 mmol) was stirred in $CH_2Cl_2$/HOAc (2:1, 9 mL) at room temperature under an argon atmosphere for 32 hours, then diluted with $H_2O$ (20 mL), and extracted with $Et_2O$ (3×50 mL). The combined ethereal extracts were washed with $H_2O$, brine, dried over $Na_2SO_4$, and evaporated in vacuo. Purification via $SiO_2$ column chromatography afforded acetylene 24 (140 mg, 41%) as a colorless oil. $^1$H NMR ($CDCl_3$, 250 MHz): δ 1.05 (s, 9H), 1.41–1.60 (m, 6H), 1.72 (quintet, J~7.2 Hz, 2H), 1.97–2.19 (m, 4H), 2.31 (t, J~7.3 Hz, 2H), 2.68–2.84 (m, 4H), 2.85–2.98 (m, 2H), 3.63 (t, J~7.1 Hz, 2H), 3.65 (s, 3H), 5.29–5.50 (m, 6H), 7.33–7.48 (m, 6H), 7.63–7.72 (m, 4H); TLC: $SiO_2$, $Et_2O$/hexane (1:1), $R_f$~0.53.

A mixture of silyl methyl ester 24 (140 mg, 0.245 mmol) and n-tetrabutylammonium fluoride (1.2 mL of 1 M soln, 1.2 mmol) in anhydrous THF (5 mL) was stirred at 0° C. under an argon atmosphere for 12 hours, then evaporated to dryness in vacuo. The residue was dissolved in EtOAc (50 mL) and washed with $H_2O$ (30 mL), brine (30 mL), dried over $Na_2SO_4$, and evaporated in vacuo. Purification of the residue via $SiO_2$ column chromatography gave hydroxyester 25 (50 mg, 62%) as a labile, colorless oil. $^1$H NMR ($CDCl_3$, 250 MHz): δ 1.36–1.67 (m, 6H), 1.72 (quintet, J~7.3 Hz, 2H), 2.02–2.24 (m, 4H), 2.33 (t, J~7.5 Hz, 2H), 2.75–2.88 (m, 4H), 2.89–3.00 (m, 2H), 3.65 (t, J~6.8 Hz, 2H), 3.67 (s, 3H), 5.30–5.53 (m, 6H); TLC: $SiO_2$, EtOAc/hexane (1:3), $R_f$~0.14.

Ester 25 (4.8 mg, 0.014 mmol) and LiOH (72 μl of a 1 M soln, 0.072 mmol) were stirred at room temperature in THF/$H_2O$ (5:2, 1.5 mL) under an argon atmosphere for 12 hours. The reaction mixture was adjusted to pH 6.5 with 1 M oxalic acid and extracted thrice with EtOAc. The combined organic extracts were washed with $H_2O$, brine, dried over $Na_2SO_4$, and evaporated in vacuo to afford acetylenic acid 26 (4.7 mg, >95%) as a labile, colorless oil. $^1$H NMR ($CDCl_3$, 250 MHz): δ 1.35–1.65 (m, 6H), 1.71 (quintet, J~7.3 Hz, 2H), 2.02–2.24 (m, 4H), 2.37 (t, J-7.3 Hz, 2H), 2.70–2.88 (m, 4H), 2.39–2.99 (m, 2H), 3.67 (t, J~6.4 Hz, 2H), 5.28–5.54 (m, 6H); TLC: $SiO_2$, EtOAc/hexane (3:7), $R_f$~0.15.

Figure 8D:
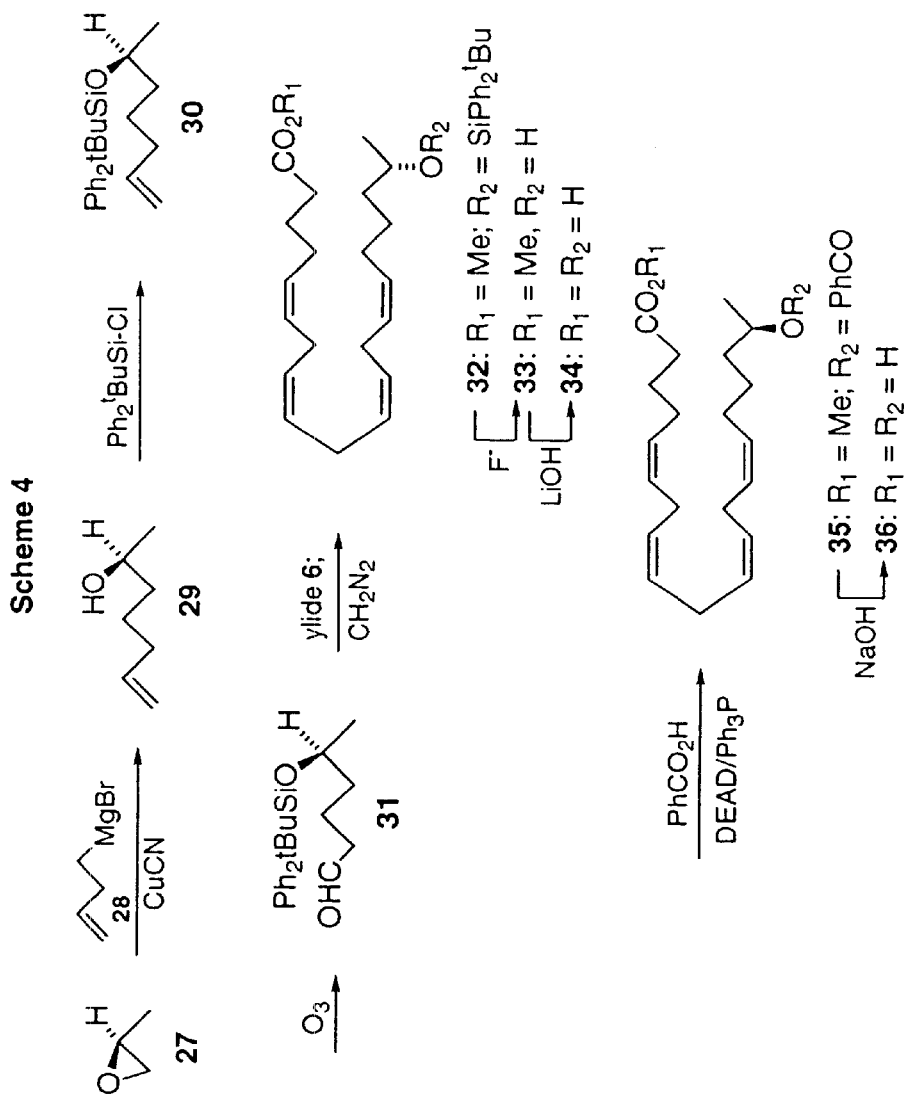

Preparation of 19(S)-HETE (34) and 19(R)-HETE (36): An ethereal solution (2 mL) of 4-bromobutene (1.31 g, 9.76 mmol) was added dropwise to a suspension of freshly activated magnesium turnings (238 mg, 9.79 mmol) in $Et_2O$ (7 mL) at 0° C. (Scheme 4; FIG. 8D). The reaction was warmed to room temperature and maintained for 3 hours. The resultant homogenous, pale yellow solution of Grignard 28 was transferred via canula under positive nitrogen pressure to a stirring suspension of CuCN (88 mg, 0.98 mmol) in dry THF (10 mL) at −20° C. After 20 minutes, (S)-(−)-propylene oxide (27) (94.6 mg, 1.62 mmol) was added neat to the homogenous cuprate solution which was then allowed to stir at 0° C. for 12 hours. The reaction was quenched using saturated aq. $NH_4Cl$ solution and extracted with EtOAc (3×10 mL). The combined organic extracts were washed with $H_2O$ (2×10 mL), brine (50 mL), dried over $Na_2SO_4$, and evaporated in vacuo. Purification of the residue via $SiO_2$ column chromatography provided alcohol 29 (623 mg, 81%) as a colorless oil. $^1$H NMR ($CDCl_3$, 250 MHz): δ 1.20 (d, J~6.7 Hz, 3H), 1.32–1.37 (m, 4H), 1.91–2.12 (m, 2H), 3.80–3.82 (m, 1H), 4.93–5.05 (m, 2H), 5.79–5.88 (m, 1H), TLC: $SiO_2$, $Et_2O$/hexane (1:1) $R_f$~0.52.

$AgNO_3$ (543 mg, 3.21 mmol) and tert-butylchlorodiphenylsilane (840 mg, 3.05 mmol) were added sequentially to a room temperature solution of alcohol 29 (317 mg, 2.78 mmol) in THF/pyridine (14:1, 10 mL). After 12 hours, the reaction mixture was filtered through a pad of CELITE and the filter cake was washed with $Et_2O$ (10 mL). The aqueous filtrate layer was separated, extracted with $Et_2O$ (2×10 mL), and the combined ethereal extracts were washed with saturated aqueous $CuSO_4$ solution, $H_2O$ (2×50 mL), brine (50 mL), dried over $Na_2SO_4$, and all volatiles were removed under reduced pressure. Purification of the residue via $SiO_2$ column chromatography (5% $Et_2O$/hexane) secured silyl ether 30 (820 mg, 84%) as a mobile, colorless oil. $^1$H NMR ($CDCl_3$, 400 MHz): δ 1.05 (s, 9H), 1.08 (d, J~6.4 Hz, 3H), 1.32–1.60 (m, 4H), 1.92–2.01 (m, 2H), 3.80–3.92 (m, 1H), 4.91–5.00 (m, 2H), 5.70–5.81 (m, 1H), 7.33–7.48 (m, 6H), 7.64–7.75 (m, 4H); TLC: $SiO_2$, EtOAc/hexane (1:9), $R_f$~0.9.

Ozone was bubbled through a 0° C. solution of 30 (500 mg, 1.42 mmol) in dry $CH_2Cl_2$ (5 mL) for 15 minutes, at which time TLC analysis revealed no remaining starting material. The reaction mixture was briefly flushed with argon, then excess Me$_2$S (2 mL) was added with stirring as the mixture was warmed to room temperature. After 12 hours, all volatiles were removed in vacuo and the residue was purified via SiO$_2$ column chromatography to afford aldehyde 31 (387 mg, 77%) as a colorless oil. $^1$H NMR (CDCl$_3$, 250 MHz): δ 1.05 (s, 9H), 1.08 (d, J~6.2 Hz, 3H), 1.39–1.50(m, 2H), 1.51–1.70 (m, 2H), 2.29 (dt, J~1.8 and 7.1 Hz, 2H), 3.78–3.95(m, 1H), 7.32–7.49 (m, 6H), 7.62–7.73 (m, 4H), 9.67 (t, J~1.8 Hz, 1H); TLC: SiO2, EtOAc/hexane (1:9), R$_f$~0.39.

Wittig condensation of aldehyde 31 (1.81 mg, 0.507 mmol) with ylide 6 (220 mg) and esterification of the adduct using diazomethane as described for the conversion of 12 to 7 (Scheme 1) provided adduct 32 (144 mg, 66%) as a colorless oil following PTLC purification [SiO$_2$: EtOAc/hexane (1:4), R$_f$~0.64]. $^1$H NMR (CDCl$_3$, 250 MHz): δ 1.05 (s, 9H), 1.07 (d, J~6.3 Hz, 3H), 1.30–1.49 (m, 4H), 1.72 (quintet, J~7.3 Hz, 2H), 1.90–2.03 (m, 2H), 2.05–2.15 (m, 2H), 2.33 (t, J~7.4 Hz, 2H), 2.64–2.89 (m, 6H), 3.67 (s, 3H), 3.75–3.90 (m, 1H), 5.20–5.47 (m, 8H), 7.28–7.49 (m, 6H), 7.62–7.71 (m, 4H).

Desilylation of 32 (450 mg) to give hydroxy-ester 33 (210 mg, 78%) followed the procedure described for the conversion of 7 to 8 (Scheme 1). $^1$H NMR (CDCl$_3$, 250 MHz): δ 1.20 (d, J~6.3 Hz, 3H), 1.40–1.53 (m, 4H), 1.71 (quintet, J~7.4 Hz, 2H), 2.06–2.17 (m, 4H), 2.33 (t, J~7.4, 2H), 2.74–2.88 (m, 6H), 3.68 (s, 3H), 3.75–3.86 (m, 1H), 5.32–5.49 (m, 8H); TLC: SiO$_2$, EtOAc/hexane (1:3), R$_f$~0.23.

Diethyl azodicarboxylate (DEAD) (68 mg, 0.387 mmol) was added neat to a stirring, room temperature solution of alcohol 33 (100 mg, 0.299 mmol), Ph$_3$P (102 mg, 0.389 mmol), and benzoic acid (48 mg, 0.389 mmol) in dry benzene (3 mL) under an argon atmosphere. After 2 hours, all volatiles were removed in vacuo and the residue was purified via SiO$_2$ column chromatography to give benzoate 35 (109 mg, 83%) as a colorless oil. $^1$H NMR (CDCl$_3$, 250 MHz): δ 1.37 (d, J~6.2 Hz, 3H), 1.41–1.53 (m, 2H), 1.61–1.79 (m, 4H), 2.10 (q, J~7.3 Hz, 4H), 2.32 (t, J~7.4 Hz, 2H), 2.75–2.90 (m, 6H), 3.69 (s, 3H), 5.18 (m, 1H), 5.34–5.46 (m, 8H), 7.45 (t, J~7.1 Hz, 2H), 7.56 (t, J~7.1 Hz, 1H), 8.04 (d, J~7.1 Hz, 2H); TLC: SiO$_2$, EtOAc/hexane (1:3), R$_f$~0.54.

Hydrolysis of esters 33 and 35 to the corresponding 19(S)-HETE (34) and 19(R)-HETE (36), respectively, was conducted as described for the conversion of 18 to 19 (Scheme 2; FIG. 8B).

Figure 8E:
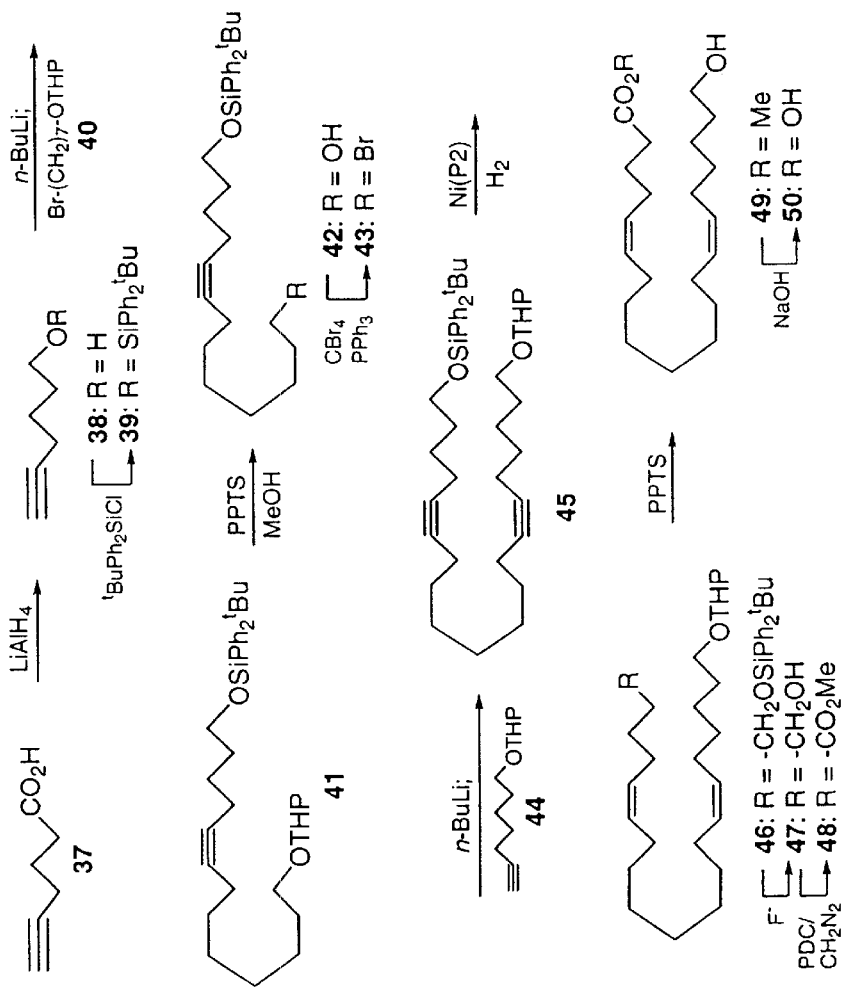
Figure 8F:
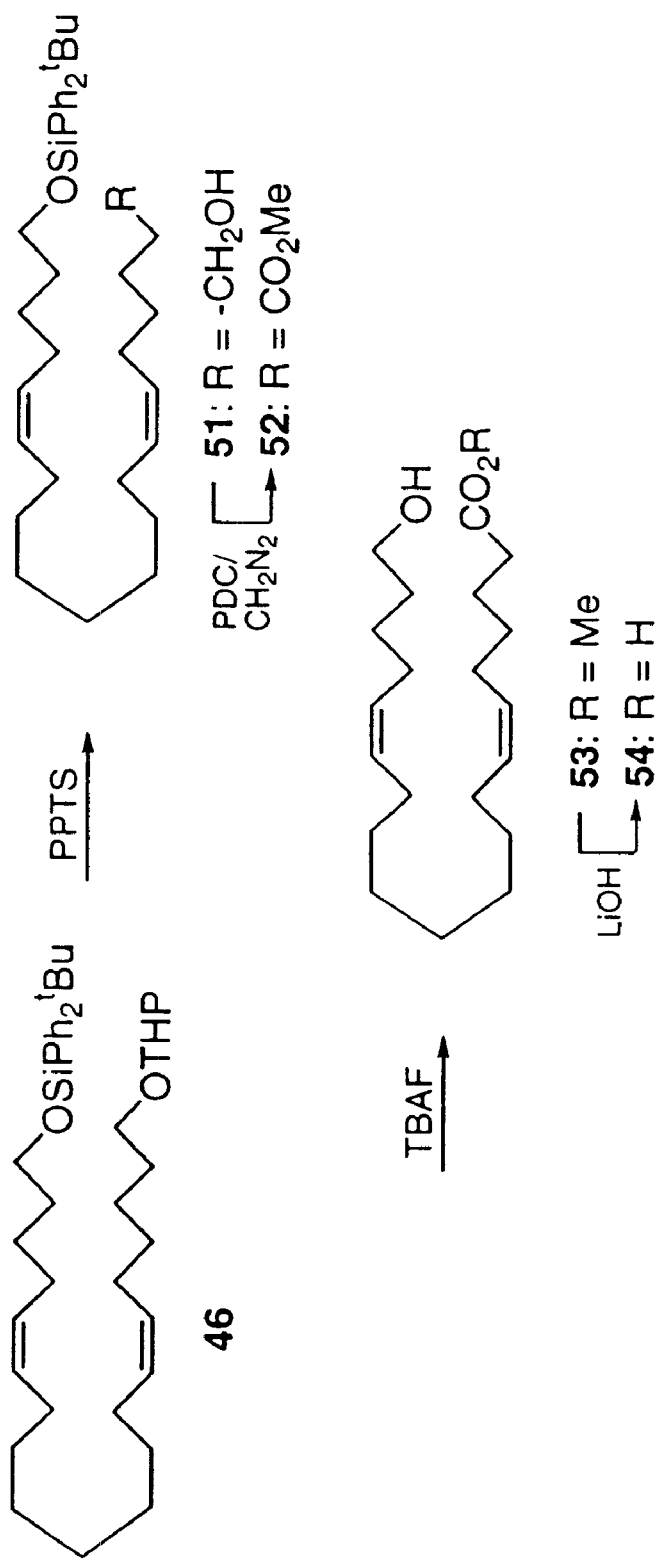

Preparation of 20-Hydroxyeicosa-5(Z),14(Z)-dienoic Acid (50): A solution of 5-hexynoic acid (37) (3.4 g, 30.35 mmol) in Et$_2$O (6 mL) was added dropwise to a stirring, 0° C. solution of LiAlH$_4$ (860 mg, 22.7 mmol) in Et$_2$O (20 mL) under argon (Scheme 5; FIG. 8E). The reaction mixture was brought to room temperature and maintained for 3 hours, then cooled to 0° C. and quenched with saturated aqueous Na$_2$SO$_4$ solution. The resultant suspension was filtered through a bed of CELITE and the filter cake was washed with Et$_2$O. The combined ethereal filtrates were dried over Na$_2$SO$_4$ and evaporated in vacuo to give 5-hexyn-1-ol (38) (3.02 9, 91%) as a colorless oil sufficiently pure to be used in the next step without further purification. $^1$H NMR (CDCl$_3$, 400 MHz): δ 3.67– 3.69 (m, 2H), 2.25 (dt, J~2.4 and 6.4 Hz, 2H), 1.96 (t, J~2.4 Hz, 1H), 1.57–1.72 (m, 4H); TLC: SiO$_2$, EtOAc/hexane (3:7), R$_f$~0.38.

tert-Butylchlorodiphenylsilane (10.1 g, 36.97 mmol) was added over 5 minutes to a room temperature solution of alcohol 38 (3.02 9, 30.81 mmol) and imidazole (2.51 g, 36.97 mmol) in CH$_2$Cl$_2$ (25 mL). After 12 hours, the reaction mixture was diluted with CH$_2$Cl$_2$ (70 mL), washed with H$_2$O, brine, dried over Na$_2$SO$_4$, and evaporated in vacuo. Purification of the residue on a SiO$_2$ column (5% EtOAc/hexane) afforded silyl ether 39 (8.4 g, 86%) as a pale yellow oil. $^1$H NMR (CDCl$_3$, 400 MHz): δ 7.65 (dd, J~1.6 and 7.6 Hz, 4H), 7.35–7.42 (m, 6H), 3.65 (t, J~6.8 Hz, 2H), 2.19–2.22 (m, 2H), 1.92–1.94 (m, 1H), 1.55–1.71 (m, 4H), 1.10 (s, 9H); TLC: SiO$_2$, EtOAc/hexane (15:85), R$_f$~0.56.

n-BuLi (0.66 mL of a 1.6 M soln in hexane, 1.05 mmol) was added dropwise to a −40° C. solution of silyl ether 39 (320 mg, 0.96 mmol) in THF (6 mL) followed by the addition of anhydrous HMPA (1.5 mL). After 1 hour, a solution of 1-bromo-7-(tetrahydropyranyloxy)heptane (Neeland, et al., *J. Org. Chem.* 59:7383–7394, 1994) (40) (291 mg, 1.05 mmol) in THF (2 mL) was slowly added. The reaction mixture was brought to room temperature over 2 hours and maintained at that temperature for 12 hours, then quenched at 0° C. using saturated aqueous NH$_4$Cl solution. The mixture was extracted thrice with Et$_2$O and the combined ethereal extracts were washed with H$_2$O, brine, dried over Na$_2$SO$_4$, and evaporated in vacuo. Purification of the residue via SiO$_2$ column chromatography (5% EtOAc/hexane) gave adduct 41 (310 mg, 63%) as a mobile oil. $^1$H NMR (CDCl3, 400 MHz): δ 7.66 (dd, J~1.6 and 7.6 Hz, 4H), 7.35–7.42 (m, 6H), 4.56–4.58 (m, 1H), 3.83–3.88 (m, 1H), 3.71–3.75 (m, 1H), 3.67 (t, J~6 Hz, 2H), 3.46–3.50 (m, 1H), 3.34–3.39 (m, 1H), 2.11–2.16 (m, 4H), 1.78–1.88 (m, 2H), 1.42–1.77 (m, 12H), 1.29–1.41 (m, 6H), 1.08 (s, 9H); TLC: SiO$_2$, EtOAc/hexane (15:85), R$_f$~0.70.

A mixture of acetylene 41 (2.01 g, 3.93 mmol) and pyridinium p-toluenesulfonate (98 mg, 0.393 mmol) in MeOH (12 mL) was stirred at room temperature for 12 hours, then concentrated in vacuo. The residue was purified via SiO$_2$ column chromatography using EtOAc/hexane (1:9) to give alcohol 42 (1.61 g, 92%) as a colorless oil. $^1$H NMR (CDCl$_3$, 400 MHz): δ 7.66 (dd, J~1.6 and 7.6 Hz, 4H), 7.35–7.41 (m, 6H), 3.67 (t, J~6.4 Hz, 2H), 3.59–3.65 (m, 2H), 2.11–2.17 (m, 4H), 1.62–1.68 (m, 2H), 1.52–1.60 (m, 4H), 1.41–1.49 (m, 2H), 1.32–1.39 (m, 6H), 1.04 (s, 9H); TLC: SiO$_2$, EtOAc/hexane (2:3), R$_f$~0.33.

Carbon tetrabromide (124 mg, 0.373 mmol), PPh$_3$ (98 mg, 0.373 mmol), and pyridine (31 μl, 0.373 mmol) were added sequentially to a 0° C. solution of alcohol 42 (140 mg, 0.311 mmol) in CH$_2$Cl$_2$ (5 mL). After 3 hours, all volatiles were removed in vacuo and the residue was purified via SiO$_2$ column chromatography (2% EtOAc/hexane) to give bromide 43 (148 mg, 91%) as a colorless oil. $^1$H NMR (CDCl$_3$, 400 MHz): δ 7.66 (dd, J~1.6 and 8 Hz, 4H), 7.35–7.41 (m, 6H), 3.67 (t, J~6.2 Hz, 2H), 3.38 (t, J~6.4 Hz, 2H), 2.11–2.16 (m, 4H), 1.84 (quintet, J~7.4 Hz, 2H), 1.62–1.67 (m, 2H), 1.55–1.61 (m, 2H), 1.31–1.48 (m, 8H), 1.04 (s, 9H); TLC: SiO$_2$, EtOAc/hexane (1:9), R$_f$~0.58.

n-BuLi (0.45 mL of a 1.6 M soln in hexane, 0.72 mmol) was added dropwise to a −40° C. solution of 7-(tetrahydropyran-2-yloxy)-1-heptyne (Bestmann, H. J., et al., *Synthesis* 1239–1241, 1992) (44) (60 mg, 0.65 mmol) in THF (8 mL) and HMPA (2 mL) under an argon atmosphere. After 1 hour, a solution of bromide 43 (376 mg, 0.72 mmol) in THF (1 mL) was introduced and the reaction mixture was then warmed to room temperature over 1 hour. Following an additional 16 hours at ambient, the reaction was quenched with saturated aqueous NH$_4$Cl solution and extracted with Et$_2$O (3×6 mL). The combined organic extracts were washed with H$_2$O, brine, dried over Na$_2$SO4, and evaporated in vacuo. Purification of the residue via SiO$_2$ column chromatography using 5% EtOAc/hexane as eluant provided bis-acetylene 45 (84 mg, 61%) as a pale yellow oil. $^1$H NMR (CDCl$_3$, 400 MHz): δ 7.66 (dd, J~1.6 and 8 Hz, 4H), 7.35–7.41 (m, 6H), 4.55–4.57 (m, 1H) 3.84–3.89 (m, 1H), 3.70–3.76 (m, 1H), 3.67 (t, J~6.2 Hz, 2H), 3.47–3.52 (m, 1H), 3.35–3.41 (m, 1H), 2.10–2.17 (m, 8H), 1.88–1.92 (m, 1H), 1.41–1.65 (m, 19H), 1.28–1.40 (m, 6H), 1.04 (s, 9H); TLC: SiO$^2$, EtOAc/hexane (1:9), R$_f$~0.7.

NaBH$_4$ (32 mg, 0.8 mmol) was added portionwise to a stirring solution of nickel(II) acetate tetrahydrate (200 mg, 0.8 mmol) in EtOH (600 mL) under a hydrogen atmosphere. After 30 minutes, 45 (5.80 g, 16 mmol) in EtOH (50 mL) was added followed by freshly distilled ethylenediamine (4.8 g). The heterogenous mixture was maintained at room temperature under hydrogen (1 atm) for 3 hours, then diluted with Et$_2$O (600 mL) and filtered through a pad of SiO$_2$. Concentration of the filtrate in vacuo yielded diene 46 (4.40 g, 84%) as a colorless oil that required no further purification. $^1$H NMR (CDCl$_3$, 400 MHz): δ.66 (dd, J~1.6 and 8 Hz, 4H), 7.35–7.41 (m, 6H), 5.30–5.35 (m, 4H), 4.55–4.57 (m, 1H), 3.70–3.76 (m, 1H), 3.65 (t, J~6.4 Hz, 2H), 3.47–3.50 (m, 1H), 3.35–3.40 (m, 1H), 1.96–2.09 (m, 8H), 1.80–1.91 (m, 1H), 1.65–1.79 (m, 1H), 1.51–1.62 (m, 8H), 1.21–1.42 (m, 16H), 1.04 (s, 9H); TLC: SiO$_2$, EtOAc/hexane (1: 9), R$_f$0. 75.

A mixture of 46 (196 mg, 0.311 mmol) and n-tetrabutylammonium fluoride (1.55 mL of a 1 M soln in THF, 1.55 mmol) in THF (4 mL) was stirred at room temperature for 3 hours, then evaporated to dryness in vacuo. Purification of the residue via SiO$_2$ column chromatography using 10% EtOAc/hexane as eluant provided alcohol 47 (102 mg, 84%) as a pale yellow oil. $^1$H NMR (CDCl$_3$, 400 MHz): δ 5.34–5.40 (m, 4H), 4.56–4.58 (m, 1H), 3.84–3.89 (m, 1H), 3.70–3.76 (m, 1H), 3.62–3.65 (m, 2H), 3.47–3.52 (m, 1H), 3.35–3.41 (m, 1H), 1.96–2.09 (m, 8H), 1.79–1.90 (m, 1H), 1.62–1.78 (m, 1H), 1.51–1.61 (m, 8H), 1.22–1.43 (m, 16H); TLC: EtOAc/hexane (3:7), R$_f$~0.52.

A solution of alcohol 47 (11.4 mg, 0.036 mmol) and pyridinium dichromate (PDC) (81 mg, 0.216 mmol) in dry DMF (1.5 mL) was stirred at room temperature for 20 hours, then diluted with H$_2$O (2 mL) and extracted with EtOAc (3×5 mL). The combined organic extracts were washed with H$_2$O, brine, dried over Na$_2$SO$_4$, and evaporated. The residue was dissolved in Et$_2$O/MeOH (4:1, 3 mL) and exposed to excess CH$_2$N$_2$ at 0° C. for 30 minutes. All volatiles were removed in vacuo and the residue was purified by PTLC [SiO$_2$, EtOAc/hexane (2:3), R$_f$~0.65] to give ester 48 (7 mg, 62%) as a colorless oil. $^1$H NMR (CDCl$_3$, 400 MHz): δ 5.35–5.41 (m, 4H), 4.56–4.58 (m, 1H), 3.84–3.89 (m, 1H), 3.70–3.76 (m, 1H), 3.66 (s, 3H), 3.47–3.52 (m, 1H), 3.35–3.41 (m, 1H), 2.31 (t, J~7.6 Hz, 2H), 1.94–2.09 (m, 8H), 1.78–1.90 (m, 1H), 1.64–1.78 (m, 1H) 1.45–1.62 (m, 6H), 1.21–1.42 (m, 16H).

A solution of the above THP-ester 48 (7 mg, 0.016 mmol) and PPTS (1 mg) was stirred in MeOH (1 mL) at room temperature. After 12 hours, the solvent was removed in vacuo and the residue was dissolved in EtOAc (4 mL), washed with H$_2$O, brine, dried and evaporated to dryness. Purification of the residue via PTLC (SiO$_2$: EtOAc/hexane (2:3), R$_f$~0.42) afforded hydroxy-ester 49 (4.3 mg, 80%) as a colorless oil. $^1$H NMR (CDCl$_3$, 400 MHz): δ 5.36–5.42 (m, 4H), 3.67 (s, 3H), 3.66 (t, J~6.8 Hz, 2H), 2.31 (t, J~7.2 Hz, 2H), 1.99–2.08 (m, 8H), 1.68 (quintet, J~7.2 Hz, 2H), 1.55–1.61 (m, 2H), 1.28–1.39 (m, 15H).

Hydrolysis of hydroxy-ester 49 (11 mg, 0.034 mmol) was achieved using NaOH (0.134 mL of a 1 M soln in H$_2$O) in THF/H$_2$O (5:1, 2 mL) at room temperature overnight. The THF was removed in vacuo and the remaining aqueous mixture was acidified to pH 4 using 1 M oxalic acid. The resultant cloudy suspension was extracted with EtOAc (3×5 mL) and the combined extracts were washed with H$_2$O, brine, dried over Na$_2$SO$_4$, and evaporated in vacuo. Purification of the residue via PTLC [SiO$_2$: EtOAc/hexane (1:1), R$_f$~0.3] gave 20-hydroxyeicosa-5(Z),14(Z)-dienoic Acid (50) (8 mg, 78%) as a pale yellow oil. $^1$H NMR (CDCl$_3$, 300 MHz): δ 5.36–5.42 (m, 4H), 3.66 (t, J~6.8 Hz, 2H), 2.35 (t, J~7.5 Hz, 2H), 1.98–2.11 (m, 8H), 1.69 (quintet, J~7.5 Hz, 2H), 1.56–1.60 (m, 2H), 1.28–1.39 (m, 15H).

Preparation of 20-Hydroxyeicosa-6(Z),15(Z)-dienoic Acid (54): A mixture of diene 46 (92 mg, 0.146 mmol) and PPTS (10 mg) in MeOH (4 mL) was maintained at room temperature overnight, concentrated in vacuo to remove the methanol, diluted with EtOAc (20 mL), washed with H$_2$O, brine, dried over Na$_2$SO$_4$, and evaporated to dryness in vacuo (Scheme 6). Purification of the residue via SiO$_2$ column chromatography gave alcohol 51 (62 mg, 79%) as a colorless oil. $^1$H NMR (CDCl$_3$, 400 MHz): δ 7.66 (dd, J~1.6 and 8 Hz, 4H), 7.35–7.41 (m, 6H), 5.36–5.42 (m, 4H), 3.61–3.67 (m, 4H), 1.96–2.09 (m, 8H), 1.55–1.66 (m, 6H), 1.22–1.41 (m, 15H), 1.04 (s, 9H); TLC: EtOAc/hexane (2:3), R$_f$~0.45.

Alcohol 51 (62 mg) was converted to ester 52 (65%) as described for the transformation of 47 to 48 (Scheme 5). $^1$H NMR (CDCl$_3$, 400 MHz): δ 7.66 (dd, J~1.6 and 8Hz, 4H), 7.35–7.41 (m, 6H), 5.35–5.42 (m, 4H), 3.66 (s, 3H), 3.63–3.66 (m, 2H), 2.31 (t, J~7.6 Hz, 2H), 1.94–2.06 (m, 8H), 1.60–1.65 (m, 2H), 1.55–1.60 (m, 2H), 1.26–1.48 (m, 14H), 1.04 (s, 9H); TLC: EtOAc/hexane (1:1), R$^f$~0.62.

Silyl-ester 52 (28 mg) was desilylated to alcohol 53 (11 mg, 80%) as described for the transformation of 46 to 47 (Scheme 5; FIG. 8E). $^1$H NMR (CDCl$_3$, 400 MHz): δ 5.35–5.42 (m, 4H), 3.66 (s, 3H), 3.62–3.65 (m, 2H), 2.31 (t, J~7.6 Hz, 2H), 1.98–2.08 (m, 8H), 1.51–1.69 (m, 4H), 1.22–1.49 (m, 15H); TLC: SiO$_2$: EtOAc/hexane (2:3), R$_f$~0.45.

Ester 53 (10 mg) was converted to acid 54 (8 mg, 78%) as described for the transformation of 49 to 50 (Scheme 5; FIG. 8E). 1H NMR (CDCl$_3$, 300 MHz): δ 5.30–5.42 (m, 4H), 3.66 (dt, J~0.9 and 6.3 Hz, 2H), 2.35 (t, J~7.2 Hz, 2H), 1.98–2.09 (m, 8H), 1.54–1.67 (m, 4H), 1.24–1.50 (m, 15H); TLC: EtOAc/hexane (1:1), R$_f$~0.3.

Preparation of 20-Hydroxyeicosanoic Acid (55) and 19-Hydroxynonadecanoic Acid (56): A mixture of ester 8b (5 mg) and 10% Pd/C (2 mg) in EtOH/EtOAc (9:1, 3 mL) was stirred under a hydrogen atmosphere (1 atm) for 8 hours. After dilution with an equal volume of Et$_2$O, the reaction mixture was filtered through a pad of CELITE and the filter cake was washed with Et$_2$O (4 mL). Evaporation of the combined filtrates afforded methyl 20-hydroxyeicosanoate (5 mg, 98%) as a colorless gum. $^1$H NMR (250 MHz, CDCl$_3$): (1.20–1.42 (m, 30H), 1.51–1.68 (m, 4H) 2.32 (t, J~7.3 Hz, 2H), 3.65 (t, J~6.6 Hz, 2H), 3.68 (s, 3H); TLC: EtOAc/hexanes (3:7), R$_f$~0.37.

LiOH (45 μL of a 1 M aqueous soln) was added to a stirring, room temperature solution of the above ester (5.2 mg, 0.015 mmol) in THF/H$_2$O (5:1, 1.5 mL). After 10 hours, the pH was adjusted to 4 using 1 M oxalic acid and the reaction mixture was extracted with EtOAc (3×4 mL). The combined organic extracts were evaporated in vacuo to give 20-hydroxyeicosanoic acid (55) (4.5 mg, 92%) as a solid, mp 86° C. $^1$H NMR (250 MHz, CD$_3$OD): δ 1.20–1.45 (m, 30H), 1.45–1.63 (m, 4H), 2.28 (t, J~7.4 Hz, 2H), 3.55 (t, J~6.5 Hz, 2H); TLC: EtOAc/hexanes (3:7), R$_f$~0.08. 19-Hydroxynonadecanoic Acid (56) was prepared in an analogous manner from ester 8a.

Eicosatetraen-1,20-dioic Acid: Prepared from 20-HETE (9a) in 84% yield as described in S. Manna, et al., *Tetrahedron Lett.* 24:33–36, 1983.

Statistics

Mean values±1 SEM are presented. The significance of the differences in mean values between and within groups was determined using an analysis of variance for repeated measures followed by a Duncan's multiple range test. A P value of <0.05 using a two-tailed test was considered to be significant.

Results

Effect of the position of the hyciroxyl group on the vasoconstrictor response to 20-HETE. The vasoconstrictor responses to the 20-HETE derivatives are presented in FIG. 2. In renal interlobular arterioles, 20-HETE ($10^{-8}$ to $10^{-6}$ M) produced a concentration-dependent fall in diameter (−4.3±0.8 to −22.5±1.5 μm, n=7)(FIG. 2A). The threshold concentration of 20-HETE that reduced vascular diameter was 10 nM. In contrast, 5(S)-, 8(S)-, 12(S), 15(S) and 19(S)-HETE had no significant effect on the diameter of renal interlobular arteries even at a concentration of 1 μM (FIG. 2A).

Importance of other structural features vasoconstrictor response to 20-HETE. The effects of altering the length of the carbon chain on the vasoconstrictor response to 20-HETE are presented in FIG. 2B. The 21-carbon and dimethyl derivatives were just as potent vasoconstrictors as 20-HETE. However, arachidonic acid, which lacks a hydroxyl group on the 20-carbon, the 19-carbon analog of 20-HETE and 20-carboxy-arachidonic acid had no significant effect on vascular diameter. Similarly, the saturated 20-HETE derivative in which the double bonds were eliminated to alter the tertiary structure of the molecule had no effect on vascular diameter (FIG. 2B). In contrast, the partially saturated 20-HETE derivative in which only 2 of the 4 double bonds were removed was a potent a constrictor as 20-HETE (FIG. 2B). Interestingly, reversing the positions of hydroxyl-and carboxy-groups on carbon 1 and 20 in the partially saturated, reverse 20-HETE analog eliminated agonist activity (FIG. 2B).

Figure 3B:
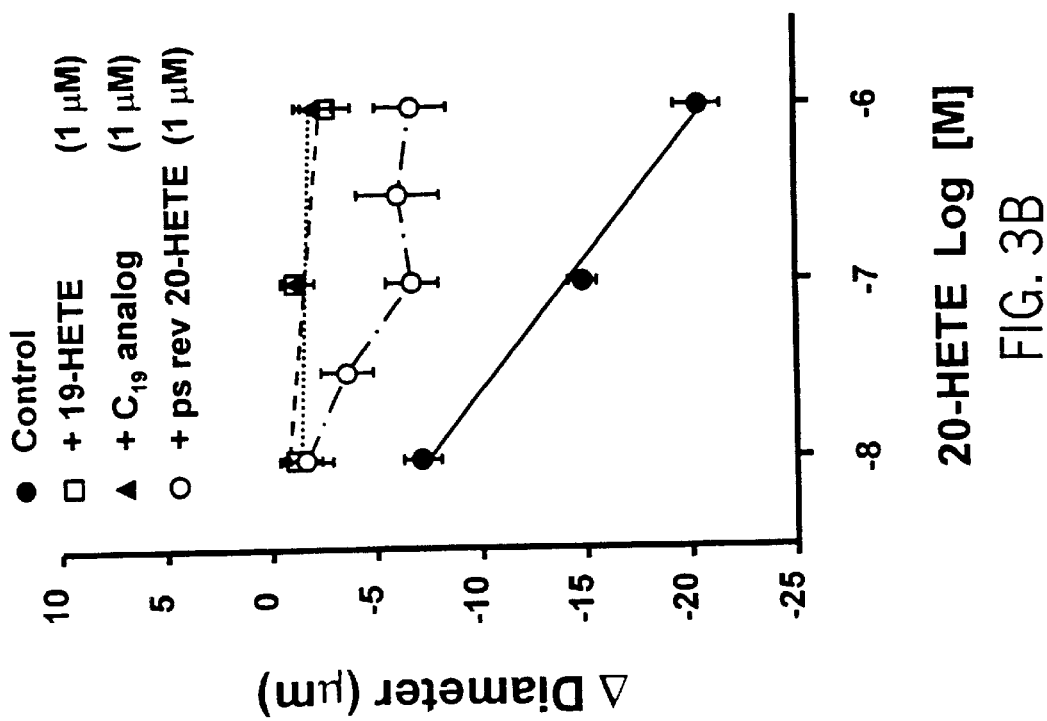
FIGS. 3A and B are graphs of antagonist activity of various analogs on the vasoconstrictor response to 20-HETE in isolated renal interlobular arteries.
Figure 3A:
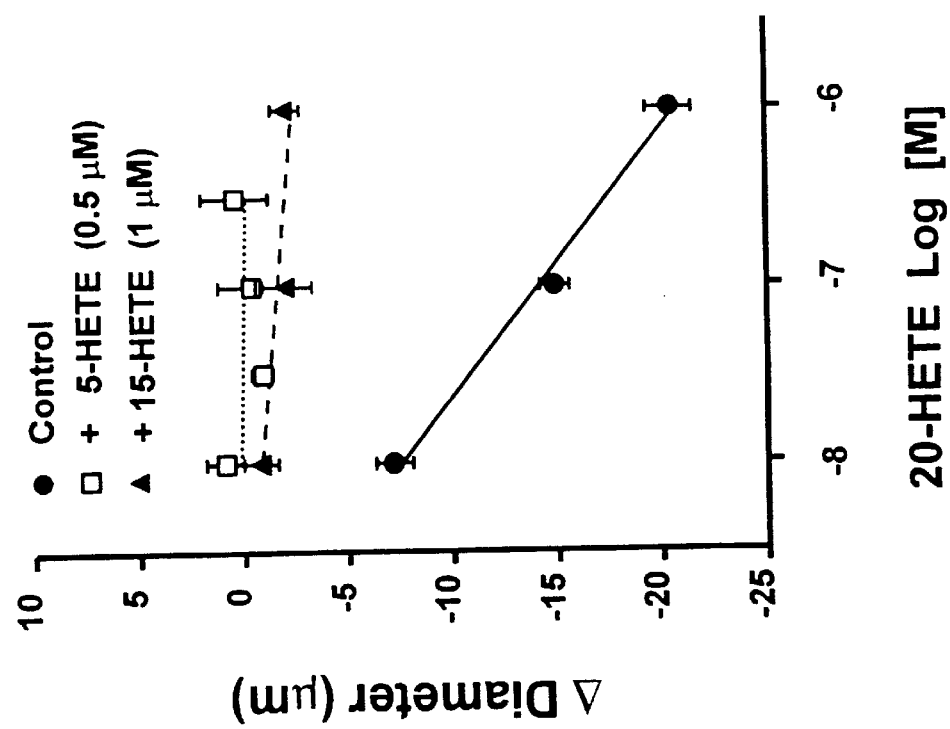

Determinants of 20-HETE antagonist activity. We also studied whether the inactive 20-HETE analogs could serve as antagonists of the vasoconstrictor response to 20-HETE. Dose response curves to 20-HETE were generated in isolated perfused renal vessels before and after adding 0.5 to 1 mM of the different analogs to the bath. Under control conditions, 20-HETE ($10^{-8}$ to $10^{-6}$ M) produce a dose-dependent fall in inner diameter (−6.4±1.2 to −21.8±1.0 μm, n=10) (FIG. 3A). Addition of 5–(n=5) or 15-HETE (n=5) to the bath completely blocked the vasoconstrictor response to 20-HETE (FIG. 3A). Similarly, after addition of 19-HETE,. the $C_{19}$-analog (n=6) or partially saturated reverse 20-HETE (n=3) to the bath completely eliminated the response to 20-HETE (FIG. 3B).

Other experiments examined the effects of moving the hydroxyl group closer to the hydrophobic head of the 20-HETE on antagonist activity. In this studies, 20-HETE ($10^{-8}$ to $10^{-6}$ M) produced a fall in vessel diameter from −5.3±0.6 to −19.2±1.9 μm (n=7) under control conditions (FIG. 4A). Addition of 8(S)- or 12(S)-HETE (1 μM) had no significant effect on the vasoconstrictor response to 20-HETE (FIG. 4A). In the presence of 8(S) -HETE, 20-HETE ($10^{-8}$ to $10^{-6}$ M) still decreased the diameter of these vessels from −2.8±0.7 to −16.9±0.2 μm (n=3).

Similarly, in the presence of 12(S)-HETE, 20-HETE ($10^{-8}$ to $10^{-6}$ M) still produced a fall in vascular diameter from −5.5±1.7 to −16.2±2.9 μm (n=5) (FIG. 4A).

Analogs of 20-HETE lacking a hydroxyl group appeared to serve as true competitive antagonists of the vasoconstrictor response to 20-HETE. For example, arachidonic acid (1 μM) reduced the vasoconstrictor response to 1 μM 20-HETE as expected by 50% (FIG. 4B). However, 20-carboxy-AA had no significant antagonistic properties (FIG. 4B).

We next evaluated whether the importance of the double bonds on 20-HETE antagonist activity. In these experiments, 20-HETE ($10^{-8}$ to $10^{-6}$ M) reduced the diameter of these vessels from −5.1±0.5 to −18.9±0.8 μm (n=10) (FIG. 4B). Addition of the saturated 19-carbon analog to the bath reduced the vasoconstrictor response to 20-HETE by about 50% (FIG. 4B). Similarly, the saturated 20-HETE derivative also exhibited competitive antagonist activity (FIG. 4B). In the presence of this compound, 20-HETE ($10^{-8}$ to $10^{-6}$ M) only reduced vascular diameter by −0.9±1.3 to −7.0±2.9 μm (n=5) (FIG. 4B).

A summary of the specific examples of compounds in which we have demonstrated agonist or antagonist activity is presented in FIG. 5. As can be seen in FIG. 5, all of the compounds described herein with known agonist and antagonist properties require a loop structure like 20-HETE with a nonpolar head and require a hydroxyl group or some other reactive group near the 20-carbon. If the compound has a hydroxy group at a distance equivalent or reactive group 5 or 6 carbons from the double bond, it is an agonist. If the OH group is located only 4 carbons from the double bond or elsewhere, it is an antagonist. From these specific examples, we derived a more general description of the structure required for agonist and antagonist activity in FIG. 6. Also shown are specific examples of related structures (FIG. 7) which would be predicted on the basis of information presented herein that should exhibit agonist or antagonist activity using the assays described herein.

Discussion

The present study examined the vascular effects of a series of analogs of 20-HETE to determine the structural determinants of the vasoconstrictor response to this compound. Our results indicate that arachidonic acid, which differs from 20-HETE by the lack of a hydroxyl group on the 20-carbon, does not constrict renal interlobular arteries. Similarly, 5-, 8-, 12-, 15- and 19-HETE in which the hydroxyl group is located on other carbons has no effect on vascular diameter. In addition, a 19-carbon derivative of 20-HETE also had no effect on vascular tone. In contrast, 21-HETE and dimethyl 20-HETE are just as potent constrictors as 20-HETE. These results indicate that the vasoconstrictor response to 20-HETE is critically dependent on the presence of a hydroxyl group on the 20 or 21 carbon.

We also examined the importance of the tertiary structure of 20-HETE to its vasoconstrictor properties. The characteristic loop structure of 20-HETE and other eicosanoids is determined by interactions between the double bonds in the molecule. Therefore, the vascular responses to saturated and partially saturated analogs of 20-HETE were compared to that of the native compound. We found that the saturated 20-HETE analog had no effect on vascular tone, whereas the partially saturated analog in which the double bonds between the 5,6 and 14,15-carbons were intact retained vasoconstrictor activity. These findings indicate that the loop structure of 20-HETE is also important to its vasoconstrictor properties.

Perhaps the most exciting finding in the present study is that analogs of 20-HETE that lack vasoconstrictor activity can serve as antagonists. In this regard, arachidonic acid, 5-, 15-, 19-HETE and the 19-HETE and the C19 analog were all very effective antagonists of the vasoconstrictor response to 20-HETE. There were also predictable structural determinants of antagonist activity. Thus, it appears that preserving the hydrophobic nature of the loop structure of 20-HETE is critical to antagonist activity. For example, molecules like 12- or 8-HETE, which have a hydroxyl group near the head of the molecule, could not interact with the putative 20-HETE binding site and did not antagonize the vasoconstrictor response to 20-HETE. From this, one would predict that 11(S)- and 7(S)-HETE and 8,9- and 11,12-EETs and DiHetes would all be ineffective as 20-HETE antagonists.

We also found that the double bonds and the intact loop structure of the 20-HETE analogs were important determinants of antagonist activity. In this regard, saturated C19- and C20-analogs of 20-HETE were not as effective as the parent compounds in antagonizing the vasoconstrictor response to 20-HETE. Similar to our findings with analogs with agonist activity, we found that only one pair of double bonds is required to maintain antagonist activity. In this regard, a partially saturated, reverse 20-HETE analog completely blocked the vasoconstrictor response to 20-HETE. This compound is particularly interesting since it would be more biologically stable than the other analogs because removal of the double bonds across the 8,9- and 11,12- carbons would block metabolism of this compound by cyclooxygenase and lipoxygenase enzymes. Stability of this compound could also be enhanced by adding an ionizable sulfonimide group to block metabolism by β-oxidation and esterification. Addition of this group has recently been reported to enhance in vivo bioavailabilty and not alter the biological activities of 20-HETE, EETs and mechanism based inhibitors of the synthesis of 20-HETE (Imig, et al., *Hypertension* 33(Part 2):408–413, 1999).

The present finding that there are distinct structural requirements for the vasoconstrictor actions of 20-HETE and that closely-related inactive analogs serve as 20-HETE antagonists provide the first evidence for a 20-HETE receptor. The nature of this receptor however, remains to be determined. Classical receptors are generally associated with the extracellular face of the membrane and are members of the 7 transmembrane domain family of proteins. The effects of 20-HETE on potassium channel activity, vascular tone and growth and sodium transport in renal tubules is associated with activation of PKC and/or the MAP kinase tyrosine kinase activity (Sun, et al., supra, 1999). It appears that 20-HETE acts more like DAG as an intracellular lipid activator of kinase activity rather than a hormone or paracrine hormone acting on an extracellular receptor.

Recent studies have indicated that 20-HETE plays and important role as a second messenger in autoregulation of renal blood flow, tubuloglomerular feedback, renal sodium transport, pulmonary function, and the mitogenic and vasoconstrictor response to numerous vasoactive hormones and growth factors (Roman, supra, 1999). The formation of P450 metabolites of AA is altered in genetic and experimental models of hypertension (Stec, D. E., et al., *Hypertension* 271:1329–1336, 1996; Sacerdoti, D., et al., *Science* 243:388–390, 1989; Stec, D. E., et al., *Hypertension* 27:564–568, 1996), diabetes (Imaoka, S., et al., *Biochem. Biophys. Res. Comm.* 152:680–687, 1988), hepatorenal syndrome (Sacerdoti, D., et al., *J. Clin. Invest.* 100:1264–1270, 1997) and toxemia of pregnancy. 20-HETE also contributes to the vasoconstrictor cations of angiotensin II, endothelin, and nitric oxide synthase inhibitors and the inhibitory effects of PTH, dopamine, AII, bradykinin, endothelin, vasopressin and TNF on sodium transport in the kidney (Roman, R. J., supra, 1999). Given the critical role of this substance in the regulation of renal and pulmonary function, vascular tone and the control of arterial pressure, it is likely that 20-HETE antagonists and stable analogs may have therapeutic potential in the treatment of some of these diseases. At very least, these analogs should provide investigators with very important, new tools to investigate 20-HETE signaling pathways and the role of this substance in the control of renal and cardiovascular function.

Uses of Analogs and Antagonists
Renal Metabolism of Arachidonic Acid by Cytochrome P450 Enzymes.

It has long been recognized that cyclooxygenase and lipoxygenase enzymes metabolize arachidonic acid (AA) and that the products formed influence both renal function and vascular tone (McGiff, J. C., *Ann. Rev. Pharmacol. Toxicol.* 31:339–369, 1991). However, in the last 10 years, a new pathway for the metabolism of AA has emerged. Indeed, recent studies have indicated that in the small blood vessels throughout the body, the glomerulus and tubules in the kidney, and in the pulmonary vasculature and airways, AA is primarily metabolized by cytochrome P450 enzymes to epoxyeicosatrienoic acids (EETs), dihydroxyeicosatrienoic acids (DiHETEs) and 19- and 20-hydroxyeicosatetraenoic acids (19- and 20-HETE). It is also now apparent that these metabolites play a central role as second messengers in the regulation of vascular tone, renal function, pulmonary function and mediates the detrimental effects of mitogens on blood vessels and the kidney in various disease states (Harder, D. R., et al., *J. Vasc. Rev.* 32:79–92, 1995; Rahman, M., et al., *Am. J. Hypertens.* 10:356–365, 1997; McGiff, J. C., supra, 1991).

Enzymes of the cytochrome P450 4A family (CYP 4A) catalyze the formation of 20-HETE. cDNAs encoding for 13 different isoforms in this family of enzymes have now been identified in various species. CYP 4A11 and CYP 4F2 are expressed in the human kidney, and CYP 4F2 appears to be the isoform primarily responsible for the formation of 20-HETE in man (Simpson, A. E. C. M., *Gen. Pharmac.* 28:351–359, 1997). Four isoforms, CYP 4A1, 4A2, 4A3, and 4A8 have been cloned from the kidneys of rats. All, except CYP 4A8, produce 20-HETE when incubated with arachidonic acid. Messages for the CYP 4A2 and 4A3 isoforms are expressed in small arterioles throughout the body, in glomeruli and renal tubules in the kidney and in airways and the vasculature of the lung. Similarly, CYP 4A protein can be detected in renal and cerebral arteries, in the kidney and in airways and the vasculature of the lung (Zhu, et al., supra, 1998; Jacobs, et al., supra, 1999). Small blood vessels, renal and lung tissues all produce 20-HETE when incubated with AA.

Many factors regulate the expression of cytochrome P450 enzymes. CYP 4A1 and 4A3 mRNA and protein are highly expressed in the kidney of neonatal rats but the levels decline into adulthood. In contrast, CYP 4A2 protein is not expressed in the kidneys of neonates, but the levels increase with age until it becomes the major isoform expressed in the kidneys of adult rats (Omata, K., et al., *Am. J. Physiol.* 262:F8–Fl6, 1992). In the proximal tubule, angiotensin II (AII) increases the formation of EETs, whereas epidermal growth factor (EGF), dopamine and parathyroid hormone (PTH) increase the formation of 20-HETE (Lin, F., supra, 1995; Ominato, M., *J. Membrane Biol.* 152:235–243, 1996; Rahman, M., et al., supra, 1997). In the TALH, a variety of peptide hormones increase the formation of 20-HETE (Frazier, L. W. and T. Yorio, *Proc. Soc. Exp. Biol. Med.* 201:229–243, 1992; McGiff, J. C., supra, 1991). The expression of CYP 4A proteins in the kidney and vasculature is downregulated in rats fed a high salt diet and this can be prevented if circulating AII levels are maintained by iv infusion. In contrast, a high salt intake increases, the expression of CYP 2C23 and the formation of EETs in the kidney (Makita, K., et al., *FASEB J.* 10:1456–1463, 1996).

Renal CYP 4A activity is increased by glucocorticoids, mineralocorticoids, and progesterone. Antilipidemic agents, such as clofibrate, induce the expression of CYP 4A1 and 3 and the synthesis of 20-HETE in the liver and kidney (McGiff, J. C., supra, 1991; Simpson, A. E. C. M., supra, 1997). Other inducers of P450 enzymes, such as phenobarbitol, 3-methylchrolantherene, and 3,4 benzo(a) pyrene, do not alter renal CYP 4A activity (Simpson, A. E. C. M., supra, 1997). A variety of important cardiovascular hormones such as AII, vasopressin and endothelin activate phospholipases and increase the synthesis and release of 20-HETE and 20-HETE contributes to the vasoconstrictor response to these agonists (Simpson, A. E. C. M., supra, 1997).

CYP 4A activity is elevated in diabetes, toxemia of pregnancy, hepatorenal syndrome, cyclosporin-induced nephrotoxicity and in various models of hypertension (Makita, K., et al., supra, 1996; Rahman, M., et al., supra, 1997). Toxemia of pregnancy, hepatorenal syndrome, cyclosporin-induced rephrotoxicity and hypertension are all diseases which are characterized by intense renal and peripheral vasoconstriction that may be mediated by an overproduction of 20-HETE in the vessels. The overproduction of 20-HETE may also act as a growth factor that produces hypertrophy of the wall of the vessel and narrows the lumen. This ultimately leads to heart attack, stroke or renal failure which are all long term consequences of these diseases. These observations suggest that inhibitors of the synthesis or antagonists of the actions of 20-HETE will have a therapeutic effect in preventing the detrimental effects of these diseases on renal and vascular function that ultimately account for much of the mortality and morbidity.

We propose that patients would be treated with a orally active long-acting 20-HETE antagonist on a daily basis to lower blood pressure and prevent narrowing of vessels.

20-HETE in the Regulation of Vascular Tone.

Small blood vessels throughout the body express CYP 4A2 mRNA and protein and avidly produce 20-HETE when incubated with AA. 20-HETE is a potent constrictor ($EC_{50}<10^{-8}$ M) of vascular smooth muscle cells. It promotes $Ca^{2+}$ entry by depolarizing renal VSM cells secondary to blockade of the $K_{Ca}$ channel and by increasing the conductance of L-type $Ca^{2+}$ channels (Harder, D. R., et al., supra, 1995). Inhibitors of the formation of 20-HETE activate the $K_{Ca}$ channel in VSM cells. This effect can be reversed by nM concentrations of 20-HETE. These findings indicate that 20-HETE is normally produced in small blood vessels throughout the body, where it serves as an intracellular second messenger that regulates of the activity of the $K_{Ca}$ channel (Zou, A. P., et al., supra, 1996).

Figure 9:
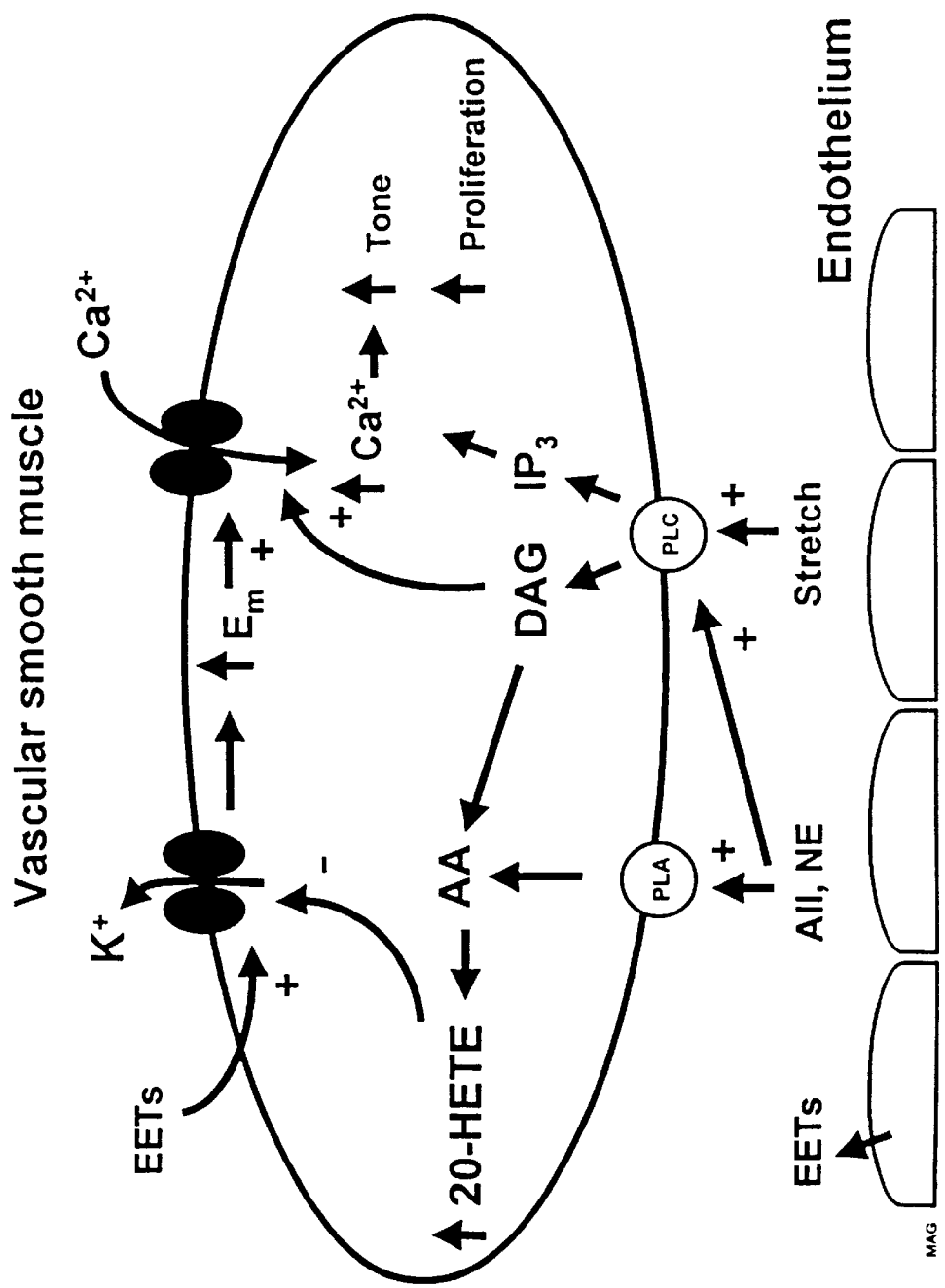
FIG. 9 is a scheme describing the actions of 20-HETE in blood vessels.
Figure 10:
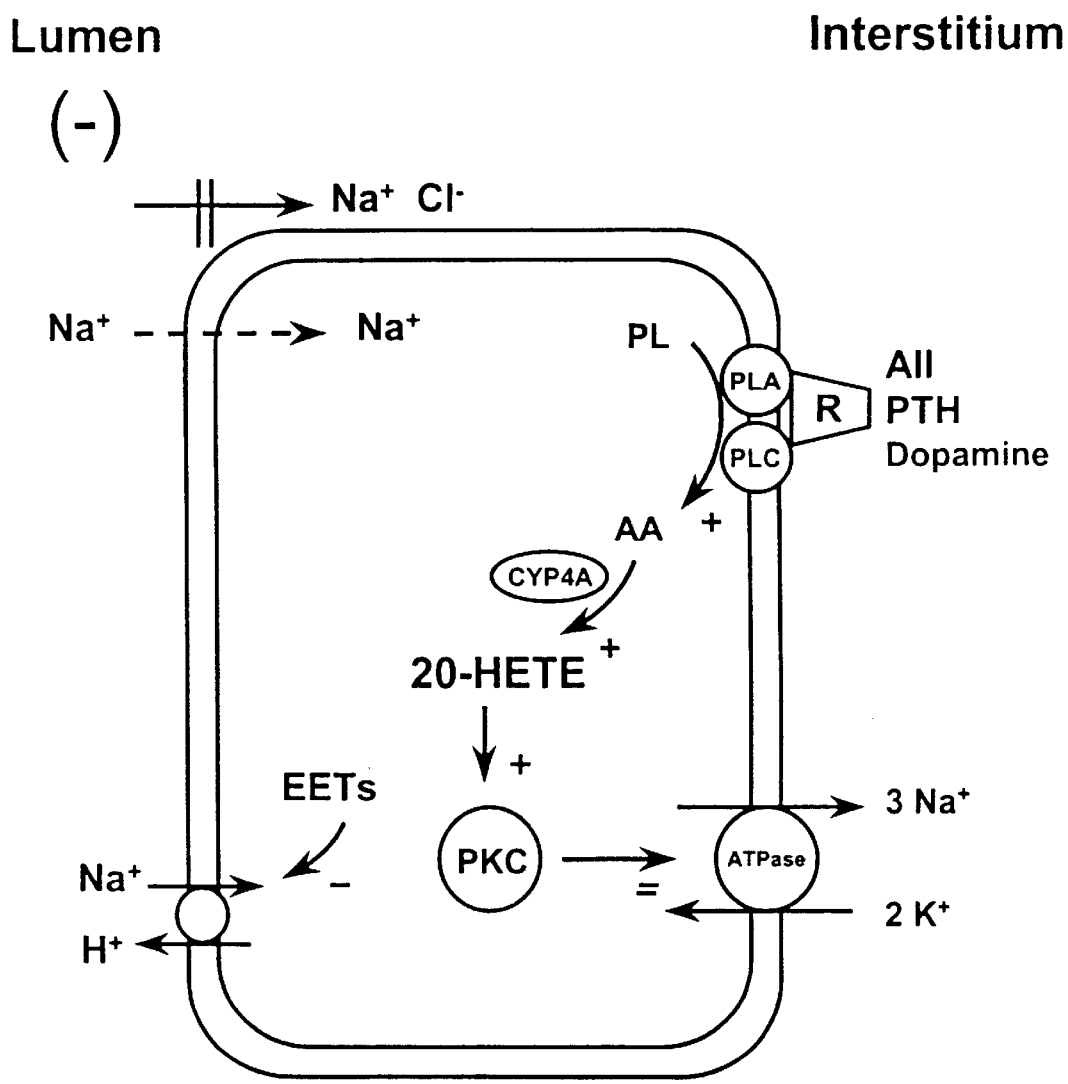
FIG. 10 is a scheme describing the action of 20-HETE in renal proximal tubule.
Figure 11:
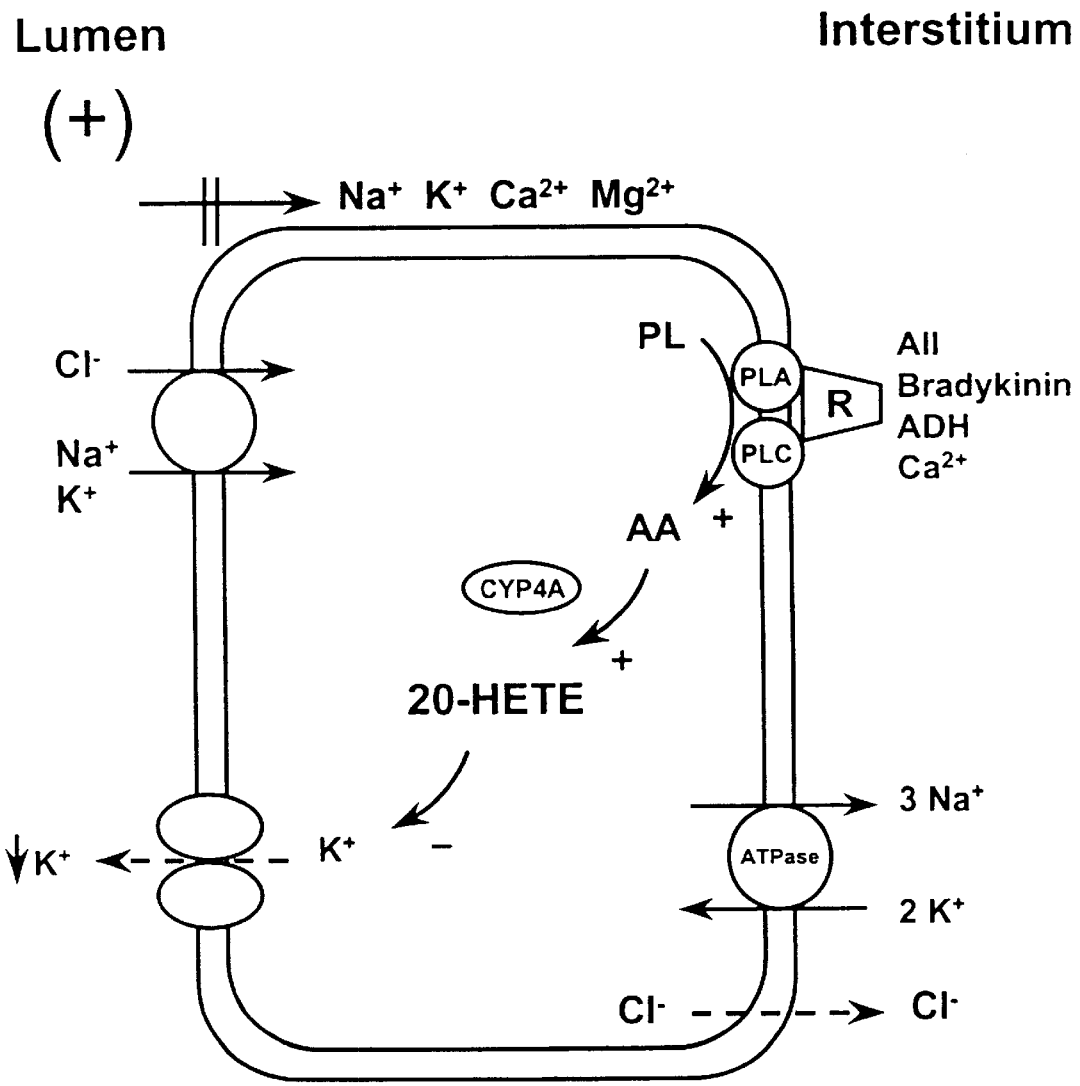
FIG. 11 is a scheme describing the action of 20-HETE in renal thick ascending loop of Henle.

A summary of the role of 20-HETE in the regulation of vascular tone is presented in FIG. 9. Membrane stretch, vasoactive hormones and mitogens activate phospholipase C and the subsequent rise in $IP_3$ triggers the release of intracellular $Ca^{2+}$ stores. However, elevations in intracellular $Ca^{2+}$ concentration should activate $K_{Ca}$ channels, leading to membrane hyperpolarization which limits $Ca^{2+}$ influx through voltage-sensitive channels. This is counterproductive and opposes vasoconstriction. Therefore, some mechanism must exist to buffer against activation of $K_{Ca}$ channels in VSM following the release of intracellular $Ca^{2+}$ stores. This is where 20-HETE is thought to play an important role. Elevations in intracellular $Ca^{2+}$ concentration activates $Ca^{2+}$-sensitive phospholipase A and DAG lipase to release arachidonic acid. Arachidonic acid is converted to 20-HETE which blocks the $K_{Ca}$ channel in renal VSM cells, leading to membrane depolarization, enhanced $Ca^{2+}$-influx, and a prolonged vasoconstrictor response. According to this scheme, 20-HETE serves as a critical second messenger that regulates the vasoconstrictor response to membrane stretch and all other vasoactive hormones and growth factors that activate phospholipases and release intracellular calcium.

There is now considerable evidence that 20-HETE plays this role in the regulation of vascular tone both in vivo and in vitro. In this regard, arachidonic acid enhances the myogenic response of isolated perfused arteries to elevations in transmural pressure, and inhibitors of the formation of 20-HETE completely block this response (Harder, D. R., et al., supra, 1995). Inhibitors of the formation of 20-HETE blocks autoregulation of renal and cerebral blood flow in vivo (Zou, A. P., et al., supra, 1994). They also attenuate the vasoconstrictor responses to vasopressin, angiotensin II, endothelin and norepinephrine both in vivo and in vitro.

20-HETE also is the mediator or a modulator of tubuloglomerular feedback (TGF) responses in the kidney. This conclusion is based on the findings that the enzyme responsible for the formation of 20-HETE is expressed in the macula densa of the kidney (Ito, O., et al., *Am. J. Physiol.* 274:F395–F414, 1998) and that 20-HETE is a potent constrictor of the renal afferent arteriole (Zou, A. P., et al., supra). The observations that addition of AA to the fluid perfusing the loop of Henle potentiates TGF responses in rats in vivo and that TGF responses are blocked by addition of P450 inhibitors to tubular perfusates further support this hypothesis. Moreover, perfusion of the loop of Henle with a solution containing 20-HETE restore TGF responses following blockade of the endogenous formation of this compound in the rat in vivo. These studies suggest that 20-HETE either serves as a mediator of TGF or acts as a second messenger at the level of the afferent arteriole to transduce the vasoconstrictor response to some other mediator released by the macula densa (Zou, A. P., et al., supra, 1994).

More recent studies have indicated that 20-HETE may also serve as a vascular oxygen sensor and mediates the changes in vascular tone associated with changes in oxygen delivery to the tissues. This conclusion is based on our findings that the production of 20-HETE in renal and cerebral arterioles is critically dependent on the oxygen tension of the incubation media (Harder, D. R., et al., supra, 1996). The Km of this reaction is 50 torr, which is on the order of the $PO_2$ found in tissues throughout the body. Moreover, recent studies by our group have indicated that inhibitors of the formation of 20-HETE and some of the 20-HETE receptor antagonists described herein, block the vasoconstrictor response to elevations in tissue $PO_2$ and whole body autoregulatory responses to elevations in tissue oxygen delivery which is central to the development of volume-dependent models of hypertension. These findings suggest that 20-HETE antagonists will have therapeutic value in the treatment of salt-sensitive forms of hypertension.

In this regard, treatment of patients with an orally active 20-HETE antagonist would block the vasoconstrictor effects of 20-HETE on blood vessels throughout the body and reduce blood pressure. It would also block the growth promotion effects of 20-HETE on the wall of the blood vessels thereby reducing narrowing of renal, cerebral and coronary arteries there produce heart attacks, stroke and other renal failure.

20-HETE-nitric Oxide Interaction in the Control of Vascular Tone.

Numerous studies have indicated that the tonic release of NO plays an important role in buffering vasoconstriction throughout the body. Although, it has generally been assumed that the vasodilator response to NO is mediated by elevations in cGMP, there is increasing evidence that NO has effects on $K^+$ channels and vascular tone that are cGMP-independent. NO binds to heme in cytochrome P450 4A enzymes and inhibits the formation of 20-HETE in renal and cerebral arterioles (Sun, et al., Supra, 1998; Alonso-Galicia, M., et al., *Am. J. Physiol.* 275:F370–F378, 1998). There is also evidence that inhibition of the formation of 20-HETE mediates the cGMP-independent effects of NO in both the renal and cerebral circulations. In this regard, NO activates the $K_{Ca}$ channel in VSM cells and dilates small blood vessels. These effects, however, are cGMP-independent because they can not be blocked by inhibitors of guanylyl cyclase or PKG (Sun C. W., et al., supra, 1998). The effects of NO on $K^+$ channels and vascular tone can be completely blocked by preventing the NO-induced fall in 20-HETE levels by adding exogenous 20-HETE to the bath. (Sun C. W., et al., supra, 1998). These findings indicate that NO inhibits the formation of 20-HETE and that this mediates the cGMP-independent component of the vasodilator response to NO by activating the $K_{Ca}$ channel in renal VSM cells (Alonso-Galicia, M., et al., supra, 1998; Sun, C. W., *Circ. Res.* 83:1–11, 1998).

In other studies, inhibitors of the formation of 20-HETE were found to block the vasodilator response to nitric oxide in the renal and cerebral circulations and the fall in blood pressure in intact animals (Alonso-Galicia, M., et al., supra, 1997). They also prevent the fall in blood pressure and cerebral blood flow hyperremia associated with induction of nitric oxide synthase in a septic shock models. These findings indicate that 20-HETE receptor antagonists will have therapeutic potential in the treatment septic shock and other inflammatory disease models associated with induction of nitric oxide synthase.

In this regard, it is known that nitric oxide is overproduced in shock and lowers blood pressure to a level that cannot sustain organ function. Since 20-HETE antagonists block the actions of NO, treatment of patients in septic shock with i.v. administration of a 20-HETE antagonist will reduce the effects of nitric oxide and restore normal blood pressure and perfusion of the heart, kidney and brain. This treatment would probably be of short-term duration (1–3 days) until the toxic agent or infection is eliminated.

The advantage of using 20-HETE antagonists rather than inhibitors of nitric oxide synthase is that the antagonists block the actions of nitric oxide at the effector site so they can be used after the patient is already in shock. Moreover, unlike inhibitors of nitric oxide synthase, the 20-HETE antagonists do not lower baseline tissue blood flow. Indeed, the profound vasoconstriction produced by NO synthase inhibitors produces profound ischemic end organ damage that precludes use of these agent for the treatment of shock.

P450 Eicosanoids in the Regulation of Renal Function.

The role of P450 metabolites of AA as second messengers in the regulation of sodium transport in various nephron segments in the kidney has also recently emerged as a dynamic new field. A summary of the effects of these compounds on sodium reabsorption in the proximal tubule is presented in Roman, et al., supra, 1999. Several laboratories have reported that 20-HETE is the primarily metabolite of AA produced by the proximal tubule and that 20-HETE inhibits Na-K-ATPase activity in this nephron segment by enhancing PKC-induced phosphorylation of the alpha subunit of Na-K-ATPase (Aperia, A., et al., *Adv. Pharmacol.* 42:870–876, 1998; Ominato, M., et al., supra, 1996).

Subsequent studies have indicated that the inhibitory effects of dopamine and PTH on Na-K-ATPase activity and sodium transport in the proximal tubule involves activation of $PLA_2$, and enhanced formation of 20-HETE. There is also evidence that P450 inhibitors can block the inhibitory effects of AII on proximal tubule reabsorption. This effect is associated with an enhanced formation of 5,6 EET, which affects the translocation of the NH3, $Na^+$—$H^+$ exchanger to the apical membrane of proximal tubule cells (Rahman, M., et al., supra, 1997).

20-HETE also plays a major role in the regulation of chloride transport in the TALH. Escalante and McGiff (McGiff, J. C., supra, 1991) first reported that 20-HETE was the major metabolite of AA produced in TALH cells and. that it inhibits $Na^+$—$K^+$-$2Cl^-$ cotransport in this nephron segment. Subsequent patch clamp studies revealed that 20-HETE blocks a 70-pS $K^+$ channel in the apical membrane of TALH cells (Wang, et al., *J. Gen. Physiol.* 106:727–743, 1995). Blockade of this channel limits $K^+$ availability for transport via the $Na^+$— $K^+$-$2Cl^-$ transporter and reduces the lumen positive transepithelial potential that serves as the main driving force for the passive reabsorption of cations ($Na^+$, $K^+$, $Ca^{2+}$ and $Mg^{2+}$) in the TALH. Consistent with this view, P450 inhibitors increase and 20-HETE decreases transepithelial potential and chloride transport in isolated TALH perfused in vitro. More recent studies have indicated that P450 inhibitors also block the inhibitory effects of AII, bradykinin, endothelin, vasopressin and elevations in intracellular $Ca^{2+}$ concentration on sodium transport in the TALH. Given the importance of 20-HETE in the regulation of sodium transport in the kidney, it is likely that stable analogs of 20-HETE would be diuretics and, thus, would have therapeutic potential in the treatment of sodium retaining states, such as congestive heart failure, pulmonary edema, hepatorenal syndrome and hypertension.

In these sodium-retaining states, characterized by edema and extracellular-volume expansion, administration of an orally active stable analog of 20-HETE would be expected to be accumulated in the kidney and inhibit tubular reabsorption of sodium and water since 20-HETE normally inhibits sodium transport in the proximal tubule and TALH. This process could be facilitated by adding a group on the carboxylic acid group to facilitate excretion of the drug into the urine by adding a glucuronide group on the first carbon. Inhibition of tubular reabsorption would increase sodium excretion, lower blood and extracelluar volume and reduce the severity of edema in these states.

Role of 20-HETE in the Pathoaenesis of Hypertension.

Several observations suggest that alteration in the renal formation of 20-HETE plays a role in the development of genetic and experimental models of hypertension. In this regard, the P4504A2 gene is selectively overexpressed in the kidneys of spontaneously hypertensive rats (SHR) (Saderoti, D., et al., supra, 1989; Stec, D., et al., supra, 1996) and this is associated with and enhanced production of 20-HETE in the kidney. Administration of inhibitors of the production of 20-HETE lowers arterial pressure in SHR and can prevent the development of hypertension (Saderoti, D., et al., supra, 1989). Since 20-HETE is a potent vasoconstrictor (Harder, D. R., et al., supra, 1995; Zou, A. P., et al., supra, 1996), 20-HETE may contribute to resetting of the pressure natriuresis relationship in SHR by elevating renal vascular resistance and TGF responses(Roman, R. J., *Am. J. Hypertension* 3:893–900, 1990). The findings that inhibitors of the 20-HETE formation reverse the elevated renal vascular tone in SHR supports this hypothesis (Imig, J., et al., *Am. J. Physiol.* 266:H1879-H1885, 1994). More recently, we also completed a genetic linkage analysis to determine wether P4504A genotype cosegregates with baseline mean arterial pressure in this population (Stec, D. F., et al., supra, 1996). However, significant linkage was detected between P4504A genotype and change in arterial pressure in F2 rats exposed to an elevated salt-inlake. These studies indicate that 20-HETE contributes to the elevation in renal and peripheral vascular tone in SHR and that P4504A genotype appears to be a determinant of salt-sensitivity in this model. These studies suggest that a 20-HETE antagonist will have antihypertensive actions and help prevent some of the ischemic glomerular injury associated with this model of hypertension.

Dahl salt-sensitive (S) rats require a high renal perfusion pressure to excrete the same amount of sodium and water as normotensive rats (Roman, R. J., et al., *Am. J. Hypertension*, 1997) and this is due to largely to an elevation in Cl⁻ transport in the thick ascending limb of the loop of Henle (Ito, et al., *Hypertension* 33(Part 2):419–423, 1999). There are now five lines of evidence that suggest an abnormality in the renal metabolism of AA by enzymes of the P4504A family may contribute to the increase in loop Cl⁻ transport and the development of hypertension in Dahl S rats. In this regard, the formation of 20-HETE and the levels of P4504A protein is reduced in the loop of Henle of Dahl S rats. (Stec, D. E., et al., supra, 1996) Administration of exogenous 20-HETE normalizes the loop Cl⁻ transport (Roman R. J., et al. supra, 1997). A genetic marker in the P4504A2 gene cosegregates with the development of hypertension in Dahl S rats, induction of renal production of 20-HETE with clofibrate prevents the development of hypertension in Dahl S rats (Stec, D. E., et al., supra, 1996) and inhibition of renal 20-HETE formation produces hypertension in a normotensive strain of rats fed a high salt diet (Stec, D. E., et al., *Hypertension* 29:315–320, 1997).

These results implicate the P4504A2 locus as a candidate gene that contributes to the alterations in renal function and development of hypertension in Dahl S rats and indicate that replacement therapy with 20-HETE agonists will have therapeutic potential in salt-sensitive hypertension. In this regard, oral administration of stable orally-active 20-HETE agonists should inhibit tubular reabsorption of sodium, increase sodium excretion, lower blood volume and blood pressure.

There is also evidence that 20-HETE contributes to the elevations in vascular tone and end organ damage associated with experimental models of hypertension. In this regard, blockade of the formation of 20-HETE attenuates the rise in arterial pressure produced by chronic administration of angiotensin II, endothelin and blockade of nitric oxide synthase. (Roman, et al., supra, 1999) Blockade of 20-HETE formation also attenuates the development of mineralocorticoid hypertension and prevents the renal damage and cardiac hypertrophy associated with this model of hypertension. Oyekan, A. D., et al., *Am. J. Physiol.* 276:R000-R000, 1999 (In press). These studies suggest that 20-HETE receptor antagonists have potential as antihypertensive agents and may provide beneficial effects on prevent renal and cardiac end organ damage in various models of hypertension.

Role of 20-HETE in the Regulation of Lung Function.

In rabbit and human lung, the effects of 20-HETE are opposite of those found in the peripheral vasculature. Jacob, E. A. et al., supra, 1999 has recently reported that human, rabbit and canine pulmonary arteries and bronchial rings all avidly produce 20-HETE when incubated with arachidonic acid. 20-HETE is a potent dilator of the pulmonary arteries and bronchiole rings. The VASO dilator response to 20-HETE is dependent on an intact endothelium and is cyclooxygenase dependent. 20-HETE either stimulates the release of vasodilatory cyclooxygenase products from pulmonary tissues or 20-HETE itself is metabolized via cyclooxygenase to a dilatory product. These studies indicate that 20-HETE and 20-HETE agonists will be useful in dilating the pulmonary vasculature in patients with pulmonary hypertension.

In human bronchiole tissue, 20-HETE agonists are potent bronchiodilators. Jacob, E. A., et al., supra, 1999. Nanomolar concentrations of these agonists completely block the elevation in bronchiolar tone produced by carbachol, which is the standard clinical test for asthma. These studies indicate that stable 20-HETE agonists will be useful as inhalational bronchodilators for the treatment of asthma. They may be especially useful in patients resistant to the bronchodilator effects of other agents (β-agonists, steroids) used in asthma inhalers.

Mitogenic Actions of 20-HETE.

Besides regulating vascular tone and renal sodium transport, there is increasing evidence that 20-HETE mediates the mitogenic actions of vasoactive agents and growth factors both in the kidney and vascular tissue. In this regard, EETs and 20-HETE increase thymidine incorporation in a variety of cell types. P450 inhibitors attenuate the growth responses to serum, vasopressin, EGF and phorbol esters in cultured glomerular mesangial cells. 20-HETE: (10–9 M) promotes the growth of cultured LLC-PK1 and OK cells and P450 inhibitors block the mitogenic actions of EGF in these cells (Lin, F., et al., supra, 1995). Finally, 20-HETE activates the MAP kinase signal transduction cascade and elevations in 20-HETE production mediates the mitogenic effects of EGF in cultured aortic VSM cells. (Uddin, et al., supra, 1998) These observations suggest that 20-HETE may play an important role in the proliferation of mesangial cells and the development of glomerulosclerosis associated with hypertension, diabetes and immune injury. In this regard, 20-HETE antagonists will have therapeutic potential in preventing narrowing of blood vessels that increase the incidence of stroke, heart disease and renal damage associated with diabetes, hypertension, cyclosporin nephrotoxicity and a variety of renal inflammatory diseases. Moreover, since 20-HETE mediates the mitogenic and angiogenic actions of a variety growth factors involved in tumor formation, it is, likely that the 20-HETE antagonists would be useful as anticancer drugs by preventing vascularization and or growth of neoplastic tissues.

We envision that patients will be given orally active, stable 20-HETE antagonists that will limit vascular growth and hypertrophy and prevent ischemic and organ damage in the heart, kidney and brain (heart attack, stroke and renal disease). In cancer therapy, blockade of 20-HETE pathway may limit blood vessel growth into tumors.

Summary

The role of P450 metabolites of AA in the regulation of renal function and vascular tone is a rapidly expanding field but some general concepts have already emerged. First, VSM cells produce 20-HETE and this substance serves as a second messenger that plays an critical role in the myogenic response, TGF, vascular hypertrophy and the vascular responses to vasoconstrictors and dilators by regulation K⁺ channel activity. Second, P450 metabolites of AA are avidly produced in the proximal tubule and the TALH and serve as second messengers in the regulation of sodium transport. Finally, the renal formation of P450 metabolites of AA is altered in hypertension, diabetes, hepatorenal syndrome and pregnancy. Given the importance of this pathway in the regulation of renal and vascular function and in mediating the growth promoting effects of a variety of mitogens, it is likely that P450 metabolites of AA contribute to the changes in renal function and vascular tone associated with these diseases. It is also likely that 20-HETE receptor antagonists will have broad therapeutic potential in the treatment of a variety of conditions such as septic shock, hypertension, diabetes, asthma, glomerular disease and cancer.

We claim:

1. A method of reducing a patient's vascular diameter, comprising the step of supplying to a patient in need of such reduction an effective amount of a 20-HETE agonist wherein the 20-HETE agonist is a compound of the formula:

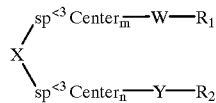

wherein $R_1$ is selected from the group consisting of carboxylic acid, phenol, amide, imide, sulfonamide, sulfonimide, active methylene, 1,3-dicarbonyl, alcohol, thiol, amine, tetrazole and other ionizable or heteroaryl groups, $R_2$ is selected from the group consisting of carboxylic acid, phenol, amide, imide, sulfonamide, sulfonimide, active methylene, 1,3-dicarbonyl, alcohol, thiol, amine, tetrazole and other ionizable or heteroaryl groups, W is a carbon chain ($C_1$ through $C_{25}$) and may be linear, cyclic, or branched and may comprise heteroatoms, Y is a carbon chain ($C_1$ through $C_{25}$) and may be linear, cyclic, or branched and may comprise heteroatoms, $sp^{<3}$ Center is selected from the group consisting of vinyl, aryl, heteroaryl, cyclopropyl, and acetylenic moieties, X is an alkyl chain that may be linear, branched, cyclic or polycyclic and may comprise heteroatoms, m is 0, 1, 2, 3, 4 or 5, and n is 0, 1, 2, 3, 4 or 5.

2. A method of treating a patient, wherein the patient is suffering from cerebral vascular injury, vasospasm, migraine or cluster headaches, stroke or cocaine-induced vasospasm, comprising treating the patient with an amount of 20-HETE antagonist effective to increase blood flow and relieve symptoms wherein the 20-HETE antagonist is a compound of the formula:

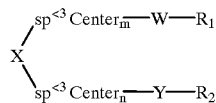

wherein $R_1$ is selected from the group consisting of carboxylic acid, phenol, amide, imide, sulfonamide, sulfonimide, active methylene, 1,3-dicarbonyl, alcohol, thiol, amine, tetrazole and other ionizable or heteroaryl groups, $R_2$ is selected from the group consisting of carboxylic acid, phenol, amide, imide, sulfonamide, sulfonimide, active methylene, 1,3-dicarbonyl, alcohol, thiol, amine, tetrazole and other ionizable or heteroaryl groups, W is a carbon chain ($C_1$ through $C_{25}$) and may be linear, cyclic, or branched and may comprise heteroatoms, Y is a carbon chain ($C_1$ through $C_{25}$) and may be linear, cyclic, or branched and may comprise heteroatoms, $sp^{<3}$ Center is selected from the group consisting of vinyl, aryl, heteroaryl, cyclopropyl, an d acetylenic moieties, X is an alkyl chain that may be linear, branched, cyclic or polycyclic and may comprise heteroatoms, m is 0, 1, 2, 3, 4 or 5, and n is 0, 1, 2, 3, 4 or 5.

3. The method of claim 2 wherein the compound has a carboxyl or other ionizable group at either $R_1$ or $R_2$ and wherein the compound comprises a double bond or other functional group at a distance equal to 14–15 carbons from the ionizable group.

4. The method of claim 3 wherein the compound is a 20-HETE antagonist and wherein the compound comprises a length of 19–21 carbons, has a pair of double bonds and does not have a hydroxyl group on the 20–21 carbon at either $R_1$ or $R_2$.

5. The method of claim 4 wherein the compound is selected from the group consisting of 5(S)-HETE, 15(S)-HETE, 19(S)-HETE, 19-hydroxynonadeca-5(Z),8(Z),11(Z),14(Z)-tetraenoic acid and 20-hydroxyeicosa 6(Z),15(Z)-dienoic acid.

6. The method of claim 1, wherein the compound comprises a length of 20–21 carbons, has a carboxyl or other ionizable group at either $R_1$ or $R_2$, comprises a double bond or other functional group at a distance equal to 14–15 carbons from the ionizable group, and comprises a pair of double bonds and a hydroxyl group on the 20 or 21 carbon at either $R_1$ or $R_2$.

7. The method of claim 6 wherein the compound is selected from the group consisting of 21–HETE, ps20-HETE and dimethyl 20–-HETE.

8. The method of claim 6 wherein the compound provides a diuretic effect.

9. The method of claim 8 wherein the patient has a condition selected from the group of congestive heart failure, pulmonary edema, hepatorenal syndrome and hypertension.

10. The method of claim 6 wherein the patient has salt sensitive form of hypertension.

11. The method of claim 6 wherein the patient has asthma and the compound is delivered as an inhalational therapy.

12. The method of treating septic shock or other inflammatory disease associated with induction of NOn synthase comprising treating a patient suffering therefrom with an amount of 20-HETE antagonist sufficient to reduce disease symptoms wherein the 20-HETE antagonist is a compound of the formula:

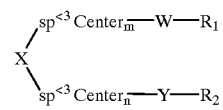

wherein $R_1$ is selected from the group consisting of carboxylic acid, phenol, amide, imide, sulfonamide, sulfonimide, active methylene, 1,3-dicarbonyl, alcohol, thiol, amine, tetrazole and other ionizable or heteroaryl groups, $R_2$ is selected from the group consisting of carboxylic acid, phenol, amide, imide, sulfonamide, sulfonimide, active methylene, 1,3-dicarbonyl, alcohol, thiol, amine, tetrazole and other ionizable or heteroaryl groups, W is a carbon chain ($C_1$ through $C_{25}$) and may be linear, cyclic, or branched and may comprise heteroatoms, Y is a carbon chain ($C_1$ through $C_{25}$) and may be linear, cyclic, or branched and may comprise heteroatoms, $sp^{<3}$ Center is selected from the group consisting of vinyl, aryl, heteroaryl, cyclopropyl, and acetylenic moieties, X is an alkyl chain that may be linear, branched, cyclic or polycyclic and may comprise heteroatoms, m is 0, 1, 2, 3, 4 or 5 and n is 0, 1, 2, 3, 4 or 5.

13. A method of treating congestive heart failure, pulmonary edema, hepatorenal syndrome or hypertension comprising treating a patient suffering therefrom with an amount of a 20-HETE agonist sufficient to cause a diuretic effect wherein the 20-HETE agonist is a compound of the formula:

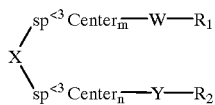

wherein $R_1$ is selected from the group consisting of carboxylic acid, phenol, amide, imide, sulfonamide, sulfonimide, active methylene, 1,3-dicarbonyl, alcohol, thiol, amine, tetrazole and other ionizable or heteroaryl groups, $R_2$ is selected from the group consisting of carboxylic acid, phenol, amide, imide, sulfonamide, sulfonimide, active methylene, 1,3-dicarbonyl, alcohol, thiol, amine, tetrazole and other ionizable or heteroaryl groups, W is a carbon chain ($C_1$ through $C_{25}$) and may be linear, cyclic, or branched and may comprise heteroatoms, Y is a carbon chain ($C_1$ through $C_{25}$) and may be linear, cyclic, or branched and may comprise heteroatoms, $sp^{<3}$ Center is selected from the group consisting of vinyl, aryl, heteroaryl, cyclopropyl, and acetylenic moieties, X is an alkyl chain that may be linear, branched, cyclic or polycyclic and may comprise heteroatoms, m is 0, 1, 2, 3, 4 or 5, and n is 0, 1, 2, 3, 4 or 5.

14. A method of treating salt-sensitive forms of hypertension comprising treating a patient suffering therefrom with an amount of a 20-HETE agonist sufficient to promote sodium excretion to reduce disease symptoms wherein the 20-HETE agonist is a compound of the formula:

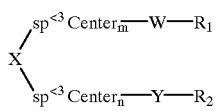

wherein $R_1$ is selected from the group consisting of carboxylic acid, phenol, amide, imide, sulfonamide, sulfonimide, active methylene, 1,3-dicarbonyl, alcohol, thiol, amine, tetrazole and other ionizable or heteroaryl groups, $R_2$ is selected from the group consisting of carboxylic acid, phenol, amide, imide, sulfonamide, sulfonimide, active methylene, 1,3-dicarbonyl, alcohol, thiol, amine, tetrazole and other ionizable or heteroaryl groups, W is a carbon chain ($C_1$ through $C_{25}$) and may be linear, cyclic, or branched and may comprise heteroatoms, Y is a carbon chain ($C_1$ through $C_{25}$) and may be linear, cyclic, or branched and may comprise heteroatoms, $sp^{<3}$ Center is selected from the group consisting of vinyl, aryl, heteroaryl, cyclopropyl, and acetylenic moieties, X is an alkyl chain that may be linear, branched, cyclic or polycyclic and may comprise heteroatoms, m is 0, 1, 2, 3, 4 or 5, and n is 0, 1, 2, 3, 4 or 5.

15. A method of treating asthma comprising treating a patient suffering therefrom with an amount of a 20-HETE agonist sufficient to reduce disease symptoms wherein the 20-HETE agonist is a compound of the formula:

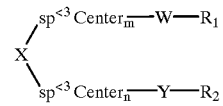

wherein $R_1$ is selected from the group consisting of carboxylic acid, phenol, amide, imide, sulfonamide, sulfonimide, active methylene, 1,3-dicarbonyl, alcohol, thiol, amine, tetrazole and other ionizable or heteroaryl groups, $R_2$ is s elected from the group consisting of carboxylic acid, pheno, amide, imide, sulfonamide, sulfonimide, active methylene, 1,3-dicarbonyl, alcohol, thiol, amine, tetrazole and other ionizable or heteroaryl groups, W is a carbon chain ($C_1$ through $C_{25}$) and may be linear, cyclic, or branched and may comprise heteroatoms, Y is a carbon chain ($C_1$ through $C_{25}$) and may be linear, cyclic, or branched and may comprise heteroatoms, $sp^{<3}$ Center is selected from the group consisting of vinyl, aryl, heteroaryl, cyclopropyl, and acetylenic moieties, X is an alkyl chain that may be linear, branched, cyclic or polycyclic and may comprise heteroatoms, m is 0, 1, 2, 3, 4 or 5, and n is 0, 1, 2, 3, 4 or 5.

16. A method of preventing vascularization or growth of neoplastic tissue comprising treating a patient in need of such prevention with an amount of a 20-HETE antagonist sufficient to reduce disease symptoms wherein the 20-HETE antagonist is a compound of the formula:

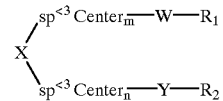

wherein $R_1$ is selected from the group consisting of carboxylic acid, phenol, amide, imide, sulfonamide, sulfonimide, active methylene, 1,3-dicarbonyl, alcohol, thiol, amine, tetrazole and other ionizable or heteroaryl groups, $R_2$ is selected from the group consisting of carboxylic acid, phenol, amide, imide, sulfonamide, sulfonimide, active methylene, 1,3-dicarbonyl, alcohol, thiol, amine, tetrazole and other ionizable or heteroaryl groups, W is a carbon chain ($C_1$–$C_{25}$) and may be linear, cyclic, or branched and may comprise heteroatoms;

Y is a carbon chain ($C_1$–$C_{25}$) and may be linear, cyclic, or branched and may comprise heteroatoms;

$sp^{<3}$ Center is selected from the group consisting of vinyl, aryl, heteroaryl, cyclopropyl, and acetylenic moieties;

X is an alkyl chain that may be linear, branched, cyclic or polycyclic and may comprise heteroatoms;

m is 0, 1, 2, 3, 4, or 5, and n is 0, 1, 2, 3, 4 or 5.

17. A method of relieving the symptoms of pulmonary hypertension comprising treating a patient suffering therefrom with a 20-HETE agonist, wherein the 20-HETE agonist is infused to dilate pulmonary circulation wherein the 20-HETE agonist is a compound of the formula:

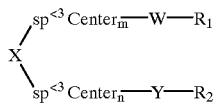

wherein $R_1$ is selected from the group consisting of carboxylic acid, phenol, amide, imide, sulfonamide, sulfonimide, active methylene, 1,3-dicarbonyl, alcohol, thiol, amine, tetrazole and other ionizable or heteroaryl groups;

$R_2$ is selected from the group consisting of carboxylic acid, phenol, amide, imide, sulfonamide, sulfonimide, active methylene, 1,3-dicarbonyl, alcohol, thiol, amine, tetrazole and other ionizable or heteroaryl groups;

W is a carbon chain ($C_1$–$C_{25}$) and may be linear, cyclic, or branched and may comprise heteroatoms;

Y is a carbon chain ($C_1$–$C_{25}$) and may be linear, cyclic, or branched and may comprise heteroatoms;

$sp^{<3}$ Center is selected from the group consisting of vinyl, aryl, heteroaryl, cyclopropyl, and acetylenic moieties, X is an alkyl chain that may be linear, branched, cyclic or polycyclic and may comprise heteroatoms, m is 0, 1, 2, 3, 4 or 5, and n is 0, 1, 2, 3, 4 or 5.

* * * * *

UNITED STATES PATENT AND TRADEMARK OFFICE
CERTIFICATE OF CORRECTION

PATENT NO. : 6,395,781 B1
DATED : May 28, 2002
INVENTOR(S) : Richard J. Roman et al.

It is certified that error appears in the above-identified patent and that said Letters Patent is hereby corrected as shown below:

<u>Title page,</u>
Item [73], Assignee, following "WI(US)" insert -- and Board of Regents, The University of Texas System, Austin, TX (US) --

Signed and Sealed this

Twenty-second Day of April, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,395,781 B1
DATED : May 28, 2002
INVENTOR(S) : Richard J. Roman et al.

It is certified that error appears in the above-identified patent and that said Letters Patent is hereby corrected as shown below:

Column 4,
Line 55, "a n bond" should read -- a $\pi$ bond --

Column 5,
Line 42, "2-HETE" should read -- 20-HETE --
Line 44, should not start a new paragraph Column 7,
Line 21, ". activation" should read -- . Activation --

Column 11,
Line 54, "65%" should be -- 68% --

Column 12,
Line 57, "(1.4 9," should be -- (1.4 g, --
Line 61, "(3 9)" should be -- (3 g) --

Column 13,
Line 43, "cclorless oil" should be -- colorless oil --

Column 15,
Lines 60 and 67, "(3.02 9)" should read -- (3.02 g) --

Column 19,
Line 15, "hyciroxyl" should read -- hydroxyl --
Line 54, delete "." at end of the line Column 23,
Line 7, delete "," between "increases the"

Column 26,
Line 21, delete "." at end of the line

Column 27,
Line 13, "Salt-inlake" should be -- salt-intake --

Column 28,
Line 32, "(10-9 M)" should be -- ($10^{-9}$ M) --
Line 50, delete "," after "is" and before "likely"

UNITED STATES PATENT AND TRADEMARK OFFICE
CERTIFICATE OF CORRECTION

PATENT NO. : 6,395,781 B1
DATED : May 28, 2002
INVENTOR(S) : Richard J. Roman et al.

It is certified that error appears in the above-identified patent and that said Letters Patent is hereby corrected as shown below:

Column 30,
Line 8, "an d" should be -- and --
Line 41, "group of" should be -- group consisting of --
Line 49, "NOn" should be -- NO --

Column 32,
Line 26, "s elected" should be -- selected --

Signed and Sealed this

Twenty-sixth Day of August, 2003

JAMES E. ROGAN
*Director of the United States Patent and Trademark Office*